United States Patent
Cohen et al.

(10) Patent No.: US 10,077,463 B2
(45) Date of Patent: Sep. 18, 2018

(54) OPTICAL SELECTION OF CELLS

(71) Applicant: President and Fellows of Harvard College, Cambridge, MA (US)

(72) Inventors: Adam E. Cohen, Cambridge, MA (US); Miao-Ping Chien, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 247 days.

(21) Appl. No.: 14/995,716

(22) Filed: Jan. 14, 2016

(65) Prior Publication Data
US 2016/0208308 A1    Jul. 21, 2016

Related U.S. Application Data

(60) Provisional application No. 62/103,844, filed on Jan. 15, 2015.

(51) Int. Cl.
*C12N 5/00*    (2006.01)
*C12Q 1/24*    (2006.01)
(Continued)

(52) U.S. Cl.
CPC .............. *C12Q 1/24* (2013.01); *C07D 207/46* (2013.01); *C07D 495/04* (2013.01); *C09B 23/00* (2013.01); *C12N 5/0006* (2013.01); *C12N 5/0081* (2013.01); *G01N 21/6428* (2013.01); *G01N 33/5026* (2013.01); *G01N 33/582* (2013.01); *G01N 2021/6439* (2013.01)

(58) Field of Classification Search
None
See application file for complete search history.

(56) References Cited

U.S. PATENT DOCUMENTS 5,290,699 A    3/1994 Oesterhelt et al.
5,661,035 A    8/1997 Tsien et al.
(Continued)

FOREIGN PATENT DOCUMENTS

EP    1 970 446 A1    9/2008
EP    2 023 127 A1    2/2009
(Continued)

OTHER PUBLICATIONS

Invitation to Pay Additional Fees for PCT/US2012/066303, dated Mar. 21, 2013.
(Continued)

*Primary Examiner* — Robert J Yamasaki
*Assistant Examiner* — Charles Z Constantine
(74) *Attorney, Agent, or Firm* — Wolf, Greenfield & Sacks, P.C.

(57) ABSTRACT

Provided herein are photochemical crosslinkers and photocleavable crosslinkers and their uses in methods for cell selection from cell cultures. The photochemical crosslinkers comprise a fluorescent dye and a radical generator. The photocleavable crosslinkers comprise a photocleavable linker linking two electrophilic groups to each other. Also provided are systems for imaging cells comprising a plurality of cells crosslinked to extracellular matrix proteins using a crosslinker as described, an imaging apparatus, an illuminating apparatus, and software for image processing.

23 Claims, 14 Drawing Sheets
Specification includes a Sequence Listing.

(51) Int. Cl.

| | | |
|---|---|---|
| C07D 207/46 | (2006.01) | |
| C07D 495/04 | (2006.01) | |
| G01N 21/64 | (2006.01) | |
| G01N 33/58 | (2006.01) | |
| C09B 23/00 | (2006.01) | |
| G01N 33/50 | (2006.01) | |

(56) References Cited

U.S. PATENT DOCUMENTS

| | | | |
|---|---|---|---|
| 5,925,523 | A | 7/1999 | Dove et al. |
| 6,107,066 | A | 8/2000 | Tsien et al. |
| 6,200,759 | B1 | 3/2001 | Dove et al. |
| 6,243,197 | B1 | 6/2001 | Schalz |
| 6,885,492 | B2 | 4/2005 | DeSimone et al. |
| 6,898,004 | B2 | 5/2005 | Shimizu et al. |
| 6,972,892 | B2 | 12/2005 | DeSimone et al. |
| 6,991,910 | B2 | 1/2006 | Adorante et al. |
| 7,459,333 | B2 | 12/2008 | Richards et al. |
| 7,560,709 | B2 | 7/2009 | Kimura et al. |
| 7,736,897 | B2 | 6/2010 | Tao et al. |
| 7,964,853 | B2 | 6/2011 | Araya |
| 8,202,699 | B2 | 6/2012 | Hegemann et al. |
| 8,273,722 | B2 | 9/2012 | Ladine et al. |
| 8,401,609 | B2 | 3/2013 | Deisseroth et al. |
| 8,532,398 | B2 | 9/2013 | Filkins et al. |
| 8,562,658 | B2 | 10/2013 | Shoham et al. |
| 8,580,937 | B2 | 11/2013 | Spudich et al. |
| 8,603,790 | B2 | 12/2013 | Deisseroth et al. |
| 8,617,876 | B2 | 12/2013 | Farrar et al. |
| 8,647,870 | B2 | 2/2014 | Hegemann et al. |
| 8,716,447 | B2 | 5/2014 | Deisseroth et al. |
| 9,057,734 | B2 | 6/2015 | Cohen et al. |
| 9,207,237 | B2 | 12/2015 | Cohen et al. |
| 9,518,103 | B2 | 12/2016 | Cohen et al. |
| 9,702,874 | B2 | 7/2017 | Cohen et al. |
| 9,791,455 | B2 | 10/2017 | Cohen et al. |
| 2002/0021490 | A1 | 2/2002 | Kasahara et al. |
| 2005/0202398 | A1 | 9/2005 | Hegemann et al. |
| 2007/0087959 | A1 | 4/2007 | Sfeir et al. |
| 2009/0142852 | A1 | 6/2009 | Friedrich et al. |
| 2009/0229669 | A1 | 9/2009 | Birge et al. |
| 2009/0268511 | A1 | 10/2009 | Birge et al. |
| 2010/0120043 | A1 | 5/2010 | Sood et al. |
| 2011/0165681 | A1 | 7/2011 | Boyden et al. |
| 2011/0200568 | A1 | 8/2011 | Ikeda et al. |
| 2012/0258451 | A1* | 10/2012 | Klimanskaya ....... C12N 5/0621 435/6.1 |
| 2013/0170026 | A1 | 7/2013 | Cohen et al. |
| 2013/0224756 | A1 | 8/2013 | Cohen et al. |
| 2014/0093907 | A1 | 4/2014 | Miller et al. |
| 2014/0120557 | A1 | 5/2014 | Xie et al. |
| 2014/0135382 | A1 | 5/2014 | Spudich et al. |
| 2014/0295413 | A1 | 10/2014 | Cohen et al. |
| 2015/0004637 | A1 | 1/2015 | Cohen et al. |
| 2015/0285820 | A1 | 10/2015 | Cohen et al. |
| 2015/0369740 | A1 | 12/2015 | Cohen et al. |
| 2016/0069876 | A1 | 3/2016 | Cohen et al. |
| 2017/0313757 | A1 | 11/2017 | Cohen et al. |

FOREIGN PATENT DOCUMENTS

| | | | |
|---|---|---|---|
| EP | 2 112 510 A1 | 10/2009 | |
| JP | 2007269973 A * | 10/2007 | |
| JP | 2009-018772 A | 1/2009 | |
| JP | 2009-065848 A | 4/2009 | |
| JP | 2010-538603 A | 12/2010 | |
| JP | 2012-014066 A | 1/2012 | |
| WO | WO 01/59446 A2 | 8/2001 | |
| WO | WO 01/83701 A2 | 11/2001 | |
| WO | WO 2004/063326 A2 | 7/2004 | |
| WO | WO 2007/019398 A1 | 2/2007 | |
| WO | WO 2007/131180 A2 | 11/2007 | |
| WO | WO 2007/139201 A1 | 12/2007 | |
| WO | WO 2008/149055 A1 | 12/2008 | |
| WO | WO 2010/027446 A2 | 3/2010 | |
| WO | WO 2010/056970 A2 | 5/2010 | |
| WO | WO 2012/027358 A1 | 3/2012 | |
| WO | WO-2013107211 A1 * | 7/2013 | ............ C12M 25/00 |

OTHER PUBLICATIONS

International Search Report and Written Opinion for PCT/US2012/066303, dated May 28, 2013.
International Preliminary Report on Patentability for PCT/US2012/066303, dated Jun. 5, 2014.
International Search Report and Written Opinion for PCT/US2011/048793, dated Dec. 13, 2011.
International Preliminary Report on Patentability for PCT/US2011/048793, dated Mar. 7, 2013.
Invitation to Pay Additional Fees for PCT/US2015/036181, dated Oct. 27, 2015.
International Search Report and Written Opinion for PCT/US2015/036181, dated Jan. 11, 2016.
International Preliminary Report on Patentability for PCT/US2015/036181, dated Dec. 29, 2016.
Invitation to Pay Additional Fees for PCT/US2016/013384, dated Mar. 30, 2016.
International Search Report and Written Opinion for PCT/US2016/013384, dated Jun. 6, 2016.
International Preliminary Report on Patentability for PCT/US2016/013384, dated Jul. 27, 2017.
GENBANK submission, Accession No. AAA72184.1. Apr. 27, 1993. Last accessed Dec. 1, 2015.
GENBANK Submission; NIH/NCBI, Accession No. AAY82897. Ewers et al., Jun. 1, 2006. 1 page.
GENBANK Submission; NIH/NCBI, Accession No. NC_010364.1. Pfeiffer et al., Jun. 10, 2013. 1 page.
GENBANK Submission; NIH/NCBI, Accession No. P29563. Uegaki et al., Oct. 29, 2014. 3 pages.
GENBANK Submission; NIH/NCBI, Accession No. P69051. Sugiyama et al., Oct. 29, 2014. 3 pages.
GENBANK Submission; NIH/NCBI, Accession No. P96787. Ihara et al., Oct. 29, 2014. 3 pages.
GENBANK Submission; NIH/NCBI, Accession No. Z35086.1. Seidel et al., Sep. 9, 2004. 2 pages.
GENBANK Submission; NIH/NCBI, Accession No. AAG01180. Idnurm et al., Mar. 21, 2001. 1 page.
GENBANK Submission; NIH/NCBI, Accession No. AAG42454. Wang et al., Dec. 26, 2000. 1 page.
GENBANK Submission; NIH/NCBI, Accession No. AF349981. Béjà et al., May 11, 2004. 1 page.
GENBANK Submission; NIH/NCBI, Accession No. AF349983. Béjà et al., May 11, 2004. 1 page.
GENBANK Submission; NIH/NCBI, Accession No. BAA06678. Tateno et al., Feb. 7, 1999. 1 page.
GENBANK Submission; NIH/NCBI, Accession No. GU045593.1. Chow et al., Jan. 6, 2010. 1 page.
GENBANK Submission; NIH/NCBI, Accession No. HM367071. Han et al., Apr. 13, 2011. 1 page.
GENBANK Submission; NIH/NCBI, Accession No. M11720.1. Dunn et al., Apr. 26, 1993. 1 page.
Akemann et al., Imaging neural circuit dynamics with a voltage-sensitive fluorescent protein. J Neurophysiol. Oct. 2012;108(8):2323-37. doi: 10.1152/jn.00452.2012. Epub Jul. 18, 2012.
Akemann et al., Two-photon voltage imaging using a genetically encoded voltage indicator. Sci Rep. 2013;3:2231. doi: 10.1038/srep02231.
Ataka et al., A genetically targetable fluorescent probe of channel gating with rapid kinetics. Biophys J. Jan. 2002;82(1 Pt 1):509-16.
Atasoy et al., A FLEX switch targets Channelrhodopsin-2 to multiple cell types for imaging and long-range circuit mapping. J Neurosci. Jul. 9, 2008;28(28):7025-30. doi:10.1523/JNEUROSCI.1954-08.2008.
Baker et al., Genetically encoded fluorescent sensors of membrane potential. Brain Cell Biol. Aug. 2008;36(1-4):53-67.

(56) References Cited

OTHER PUBLICATIONS

Baker et al., Three fluorescent protein voltage sensors exhibit low plasma membrane expression in mammalian cells. J Neurosci Methods. Mar. 30, 2007;161(1):32-8.

Barondeau et al., Mechanism and energetics of green fluorescent protein chromophore synthesis revealed by trapped intermediate structures. Proc Natl Acad Sci U S A. Oct. 14, 2003;100(21):12111-6. Epub Oct. 1, 2003.

Bean, The action potential in mammalian central neurons. Nat Rev Neurosci. Jun. 2007;8(6):451-65.

Béjà et al., Proteorhodopsin phototrophy in the ocean. Nature. Jun. 14, 2001;411(6839):786-9.

Béjà et al., Bacterial rhodopsin: evidence for a new type of phototrophy in the sea. Science. Sep. 15, 2000;289(5486):1902-6.

Bergo et al., Conformational changes detected in a sensory rhodopsin II—transducer complex. J Biol Chem. Sep. 19, 2003;278(38):36556-62.

Bernstein et al., Optogenetics and thermogenetics: technologies for controlling the activity of targeted cells within intact neural circuits. Curr Opin Neurobiol. Feb. 2012;22(1):61-71. doi: 10.1016/j.conb.2011.10.023. Epub Nov. 24, 2011.

Boyden et al., Millisecond-timescale, genetically targeted optical control of neural activity. Nat Neurosci. Sep. 2005;8(9):1263-8. Epub Aug. 14, 2005.

Brack et al., Picosecond time-resolved absorption and fluorescence dynamics in the artificial bacteriorhodopsin pigment BR6.11. Biophys J. Aug. 1993;65(2):964-72.

Canepari et al., Combining calcium imaging with other optical applications. Cold Spring Harbor Protocols. 2013. pbd. Top066167.

Cans et al., Positioning Lipid Membrane Domains in Giant Vesicles by Micro-organization of Aqueous Cytoplasm Mimic. J. Am. Chem. Soc., 2008;130(23):7400-7406.

Cao et al., Genetically targeted optical electrophysiology in intact neural circuits. Cell. Aug. 15, 2013;154(4):904-13. doi: 10.1016/j.cell.2013.07.027. Epub Aug. 8, 2013.

Cardin et al., Targeted optogenetic stimulation and recording of neurons in vivo using cell-type-specific expression of Channelrhodopsin-2. Nat Protoc. Feb. 2010;5(2):247-54. doi: 10.1038/nprot.2009.228. Epub Jan. 21, 2010.

Carlson et al., Circular permutated red fluorescent proteins and calcium ion indicators based on mCherry. Protein Eng Des Sel. Dec. 2013;26(12):763-72. doi: 10.1093/protein/gzt052. Epub Oct. 22, 2013.

Chanda et al., A hybrid approach to measuring electrical activity in genetically specified neurons. Nat Neurosci. Nov. 2005;8(11):1619-26. Epub Oct. 2, 2005.

Chen et al., Paired-pulse depression of unitary quantal amplitude at single hippocampal synapses. Proc Natl Acad Sci U S A. Jan. 27, 2004;101(4):1063-8. Epub Jan. 13, 2004.

Chen et al., Ultrasensitive fluorescent proteins for imaging neuronal activity. Nature. Jul. 18, 2013;499(7458):295-300. doi: 10.1038/nature12354.

Chien et al., Photostick: a method for selective isolation of target cells from culture. Chem Sci. Mar. 2015;6(3):1701-1705.

Chow et al., High-performance genetically targetable optical neural silencing by light-driven proton pumps. Nature. Jan. 7, 2010;463(7277):98-102.

Chung et al., Diagnostic potential of laser-induced autofluorescence emission in brain tissue. J Korean Med Sci. Apr. 1997;12(2):135-42.

Depry et al., Multiplexed visualization of dynamic signaling networks using genetically encoded fluorescent protein-based biosensors. Pflugers Arch. Mar. 2013;465(3):373-81. doi: 10.1007/s00424-012-1175-y. Epub Nov. 9, 2012.

DeRossi et al., Cell internalization of the third helix of the Antennapedia homeodomain is receptor-independent. J Biol Chem. Jul. 26, 1996;271(30):18188-93.

Diester et al., An optogenetic toolbox designed for primates. Nat Neurosci. Mar. 2011;14(3):387-97. doi: 10.1038/nn.2749. Epub Jan. 30, 2011.

Dioumaev et al., Photocycle of Exiguobacterium sibiricum rhodopsin characterized by low-temperature trapping in the IR and time-resolved studies in the visible. J Phys Chem B. Jun. 20, 2013;117(24):7235-53. doi: 10.1021/jp402430w. Epub Jun. 10, 2013.

Dioumaev et al., Proton transfers in the photochemical reaction cycle of proteorhodopsin. Biochemistry. Apr. 30, 2002;41(17):5348-58.

Dioumeav et al., Proton transport by proteorhodopsin requires that the retinal Schiff base counterion Asp-97 be anionic. Biochemistry. Jun. 3, 2003;42(21):6582-7.

Dooley et al., Imaging dynamic redox changes in mammalian cells with green fluorescent protein indicators. J Biol Chem. May 21, 2004;279(21):22284-93. Epub Feb. 25, 2004.

Enami et al., Crystal structures of archaerhodopsin-1 and -2: Common structural motif in archaeal light-driven proton pumps. J Mol Biol. May 5, 2006;358(3):675-85.

Flock et al., Optical properties of Intralipid: a phantom medium for light propagation studies. Lasers Surg Med. 1992;12(5):510-9.

Friedrich et al., Proteorhodopsin is a light-driven proton pump with variable vectoriality. J Mol Biol. Aug. 30, 2002;321(5):821-38.

Fromherz et al., ANNINE—6plus, a voltage-sensitive dye with good solubility, strong membrane binding and high sensitivity. Eur Biophys J. Apr. 2008;37(4):509-14.

Furuta et al., Brominated 7-hydroxycoumarin-4-ylmethyls: photolabile protecting groups with biologically useful cross-sections for two photon photolysis. Proc Natl Acad Sci U S A. Feb. 16, 1999;96(4):1193-200.

Gabriel et al., Direct observation in the millisecond time range of fluorescent molecule asymmetrical interaction with the electropermeabilized cell membrane. Biophys J. Nov. 1997;73(5):2630-7.

Giovannoni et al., Proteorhodopsin in the ubiquitous marine bacterium SAR11. Nature. Nov. 3, 2005;438(7064):82-5.

Gong et al., Imaging neural spiking in brain tissue using FRET-opsin protein voltage sensors. Nat Commun. Apr. 22, 2014;5:3674. doi: 10.1038/ncomms4674.

Gradinaru et al., Molecular and cellular approaches for diversifying and extending optogenetics. Cell. Apr. 2, 2010;141(1):154-65.

Hochbaum et al., All-optical electrophysiology in mammalian neurons using engineered microbial rhodopsins. Nat Methods. Aug. 2010;11(8):825-33. doi: 10.1038/nmeth.3000. Epub Jun. 22, 2014.

Hoffmann et al., Photoactive mitochondria: in vivo transfer of a light-driven proton pump into the inner mitochondrial membrane of Schizosaccharomyces pombe. Proc Natl Acad Sci U S A. Sep. 27, 1994;91(20):9367-71.

Hou et al., Temporal dynamics of microbial rhodopsin fluorescence reports absolute membrane voltage. Biophys J. Feb. 4, 2014;106(3):639-48. doi: 10.1016/j.bpj.2013.11.4493.

Huggins et al., Optimal experimental design for sampling voltage on dendritic trees in the low-SNR regime. J Comput Neurosci. Apr. 2012;32(2):347-66. doi: 10.1007/s10827-011-0357-5. Epub Aug. 23, 2011.

Huys et al., Efficient estimation of detailed single-neuron models. J Neurophysiol. Aug. 2006;96(2):872-90. Epub Apr. 19, 2006.

Ichas et al., Mitochondria are excitable organelles capable of generating and conveying electrical and calcium signals. Cell. Jun. 27, 1997;89(7):1145-53.

Ihara et al., Evolution of the archaeal rhodopsins: evolution rate changes by gene duplication and functional differentiation. J Mol Biol. Jan. 8, 1999;285(1):163-74.

Ingenhoven et al., Fluorescent labelled analogues of neuropeptide Y for the characterization of cells expressing NPY receptor subtypes. J Recept Signal Transduct Res. Jan.-May 1997;17(1-3):407-18.

Jin et al., Single action potentials and subthreshold electrical events imaged in neurons with a fluorescent protein voltage probe. Neuron. Sep. 6, 2012;75(5):779-85. doi: 10.1016/j.neuron.2012.06.040.

Johnson et al., Localization of mitochondria in living cells with rhodamine 123. Proc Natl Acad Sci U S A. Feb. 1980;77(2):990-4.

Kirkton et al., Engineering biosynthetic excitable tissues from unexcitable cells for electrophysiological and cell therapy studies. Nat Commun. 2011;2:300. doi: 10.1038/ncomms1302.

(56) References Cited

OTHER PUBLICATIONS

Klapoetke et al., Independent optical excitation of distinct neural populations. Nat Methods. Mar. 2014;11(3):338-46. doi: 10.1038/nmeth.2836. Epub Feb. 9, 2014.

Kleinlogel et al., A gene-fusion strategy for stoichiometric and co-localized expression of light-gated membrane proteins. Nat Methods. Nov. 6, 2011;8(12):1083-8. doi: 10.1038/nmeth.1766.

Knöpfel et al., Toward the second generation of optogenetic tools. J Neurosci. Nov. 10, 2010;30(45):14998-5004.

Kochendoerfer et al., How color visual pigments are tuned. Trends Biochem Sci. Aug. 1999;24(8):300-5.

Kolodner et al., Electric-field-induced Schiff-base deprotonation in D85N mutant bacteriorhodopsin. Proc Natl Acad Sci U S A. Oct. 15, 1996;93(21):11618-21.

Kralj et al., Electrical spiking in *Escherichia coli* probed with a fluorescent voltage-indicating protein. Science. Jul. 15, 2011;333(6040):345-8.

Kralj et al., Optical recording of action potentials in mammalian neurons using a microbial rhodopsin. Nat Methods. Nov. 27, 2012;9(1):90-5. doi: 10.1038/nmeth.1782.

Kramer et al., New photochemical tools for controlling neuronal activity. Curr Opin Neurobiol. Oct. 2009;19(5):544-52. doi: 10.1016/j.conb.2009.09.004. Epub Oct. 12, 2009.

Krauthamer et al., Action potential-induced fluorescence changes resolved with an optical fiber carrying excitation light. J Fluoresc. Dec. 1991;1(4):207-13.

Krylova et al., A versatile, bar-coded nuclear marker/reporter for live cell fluorescent and multiplexed high content imaging. PLoS One. May 14, 2013;8(5):e63286. doi: 10.1371/journal.pone.0063286. Print 2013.

Kuner et al., A genetically encoded ratiometric indicator for chloride: capturing chloride transients in cultured hippocampal neurons. Neuron. Sep. 2000;27(3):447-59.

Lam et al., Improving FRET dynamic range with bright green and red fluorescent proteins. Nat Methods. Oct. 2012;9(10):1005-12. doi: 10.1038/nmeth.2171. Epub Sep. 9, 2012.

Lanyi, Bacteriorhodopsin. Annu Rev Physiol. 2004;66:665-88.

Lanyi, Proton translocation mechanism and energetics in the light-driven pump bacteriorhodopsin. Biochim Biophys Acta. Dec. 7, 1993;1183(2):241-61.

Lenz et al., First steps of retinal photoisomerization in proteorhodopsin. Biophys J. Jul. 1, 2006;91(1):255-62.

Liang et al., Patterned Photostimulation with Digital Micromirror Devices to Investigate Dendritic Integration Across Branch Points. J Vis Exp. 2011;49:e2003. Video Article.

Liem et al., The patch clamp technique. Neurosurgery. Feb. 1995;36(2):382-92.

Lin et al., Brain tumor demarcation using optical spectroscopy; an in vitro study. J Biomed Opt. Apr. 2000;5(2):214-20.

Lin et al., Characterization of engineered channelrhodopsin variants with improved properties and kinetics. Biophys J. Mar. 4, 2009;96(5):1803-14. doi: 10.1016/j.bpj.2008.11.034.

Lundby et al., Engineering of a genetically encodable fluorescent voltage sensor exploiting fast Ci-VSP voltage-sensing movements. PLoS One. Jun. 25, 2008;3(6):e2514. doi: 10.1371/journal.pone.0002514.

Ma et al., Role of ER export signals in controlling surface potassium channel numbers. Science. Jan. 12, 2001;291(5502):316-9.

MacKinnon et al., Target Identification by Diazirine Photo-Crosslinking and Click Chemistry. Curr Protoc Chem Biol. Dec. 2009;1:55-73.

MacLaurin et al., Mechanism of voltage-sensitive fluorescence in a microbial rhodopsin. Proc Natl Acad Sci U S A. Apr. 9, 2013;110(15):5939-44. doi: 10.1073/pnas.1215595110. Epub Mar. 25, 2013.

Man et al., Diversification and spectral tuning in marine proteorhodopsins. EMBO J. Apr. 15, 2003;22(8):1725-31.

Martinac et al., Ion channels in microbes. Physiol Rev. Oct. 2008;88(4):1449-90.

Maruyama et al., Detecting cells using non-negative matrix factorization on calcium imaging data. Neural Netw. Jul. 2014;55:11-9. doi: 10.1016/j.neunet.2014.03.007. Epub Mar. 24, 2014.

Marvin et al., An optimized fluorescent probe for visualizing glutamate neurotransmission. Nat Methods. Feb. 2013;10(2):162-70. doi: 10.1038/nmeth.2333. Epub Jan. 13, 2013.

Mattis et al., Principles for applying optogenetic tools derived from direct comparative analysis of microbial opsins. Nat Methods. Dec. 18, 2011;9(2):159-72. doi: 10.1038/nmeth.1808.

Melkonian et al., A light and electron microscopic study of Scherffelia dubia, a new member of the scaly green flagellates (Prasinophyceae). Nord J Bot. 1986;6(2):235-256.

Miller et al., Optically monitoring voltage in neurons by photo-induced electron transfer through molecular wires. Proc Natl Acad Sci U S A. Feb. 7, 2012;109(6):2114-9. doi: 10.1073/pnas.1120694109. Epub Jan. 24, 2012.

Mogi et al., Aspartic acid substitutions affect proton translocation by bacteriorhodopsin. Proc Natl Acad Sci U S A. Jun. 1988;85(12):4148-52.

Molokanova et al., Bright future of optical assays for ion channel drug discovery. Drug Discov Today. Jan. 2008;13(1-2):14-22.

Muga et al., Membrane interaction and conformational properties of the putative fusion peptide of PH-30, a protein active in sperm-egg fusion. Biochemistry. Apr. 19, 1994;33(15):4444-8.

Mukamel et al., Automated analysis of cellular signals from large-scale calcium imaging data. Neuron. Sep. 24, 2009;63(6):747-60. doi: 10.1016/j.neuron.2009.08.009.

Murata et al., Phosphoinositide phosphatase activity coupled to an intrinsic voltage sensor. Nature. Jun. 30, 2005;435(7046):1239-43. Epub May 18, 2005.

Mutoh et al., Genetically engineered fluorescent voltage reporters. ACS Chem Neurosci. Aug. 15, 2012;3(8):585-92. doi: 10.1021/cn300041b. Epub Jun. 6, 2012.

Mutoh et al., Spectrally-resolved response properties of the three most advanced FRET based fluorescent protein voltage probes. PLoS One. 2009;4(2):e4555.

Nagel et al., Light activation of channelrhodopsin-2 in excitable cells of Caenorhabditis elegans triggers rapid behavioral responses. Curr Biol. Dec. 20, 2005;15(24):2279-84.

Neutze et al., Bacteriorhodopsin: a high-resolution structural view of vectorial proton transport. Biochim Biophys Acta. Oct. 11, 2002;1565(2):144-67.

Oldach et al., Genetically encoded fluorescent biosensors for live-cell visualization of protein phosphorylation. Chem Biol. Feb. 20, 2014;21(2):186-97. doi: 10.1016/j.chembiol.2013.12.012. Epub Jan. 30, 2014.

Park et al., Screening fluorescent voltage indicators with spontaneously spiking HEK cells. PLoS One. Dec. 31, 2013;8(12):e85221. doi: 10.1371/journal.pone.0085221. eCollection 2013.

Peron et al., From cudgel to scalpel: toward precise neural control with optogenetics. Nat Methods. Jan. 2011;8(1):30-4. doi: 10.1038/nmeth.f.325. Epub Dec. 20, 2010.

Perron et al., Second and third generation voltage-sensitive fluorescent proteins for monitoring membrane potential. Front Mol Neurosci. Jun. 22, 2009;2:5. doi: 10.3389/neuro.02.005.2009. eCollection 2009.

Popovic et al., The spatio-temporal characteristics of action potential initiation in layer 5 pyramidal neurons: a voltage imaging study. J Physiol. Sep. 1, 2011;589(Pt 17):4167-87. doi: 10.1113/jphysiol.2011.209015. Epub Jun. 13, 2011.

Przybylo et al., Fluorescence techniques for determination of the membrane potentials in high throughput screening. J Fluoresc. Nov. 2010;20(6):1139-57. doi: 10.1007/s10895-010-0665-6.

Pucihar et al., Measuring the induced membrane voltage with Di-8-ANEPPS. J Vis Exp. Nov. 19, 2009;(33). pii: 1659. doi: 10.3791/1659. Video Article.

Rousso et al., pKa of the protonated Schiff base and aspartic 85 in the bacteriorhodopsin binding site is controlled by a specific geometry between the two residues. Biochemistry. Sep. 19, 1995;34(37):12059-65.

Sakai et al., Design and characterization of a DNA-encoded, voltage-sensitive fluorescent protein. Eur J Neurosci. Jun. 2001;13(12):2314-8.

(56) References Cited

OTHER PUBLICATIONS

San Martin et al., Imaging mitochondrial flux in single cells with a FRET sensor for pyruvate.PLoS One. Jan. 21, 2014;9(1):e85780. doi: 10.1371/journal.pone.0085780. eCollection 2014.

Scanziani et al., Electrophysiology in the age of light. Nature. Oct. 15, 2009;461(7266):930-9. doi: 10.1038/nature08540.

Schoenenberger et al., Optimizing the spatial resolution of Channelrhodopsin-2 activation. Brain Cell Biol. Aug. 2008;36(1-4):119-27. doi: 10.1007/s11068-008-9025-8. Epub Jul. 25, 2008.

Shaner et al., A guide to choosing fluorescent proteins. Nat Methods. Dec. 2005;2(12):905-9.

Sheves et al., Controlling the pKa of the bacteriorhodopsin Schiff base by use of artificial retinal analogues. Proc Natl Acad Sci. U S A. May 1986;83(10):3262-6.

Siegel et al., A genetically encoded optical probe of membrane voltage. Neuron. Oct. 1997;19(4):735-41.

Sineshchekov et al., Light-induced intramolecular charge movements in microbial rhodopsins in intact *E. coli* cells. Photochem Photobiol Sci. Jun. 2004;3(6):548-54. Epub Mar. 18, 2004.

Sjulson et al., Rational optimization and imaging in vivo of a genetically encoded optical voltage reporter. J Neurosci. May 21, 2008;28(21):5582-93.

Soppa et al., Bacteriorhodopsin mutants of *Halobacterium* sp. GRB. II. Characterization of mutants. J Biol Chem. Aug. 5, 1989;264(22):13049-56.

St-Pierre et al., High-fidelity optical reporting of neuronal electrical activity with an ultrafast fluorescent voltage sensor. Nat Neurosci. Jun. 2014;17(6):884-9. doi: 10.1038/nn.3709. Epub Apr. 22, 2014.

Stuart et al., Active propagation of somatic action potentials into neocortical pyramidal cell dendrites. Nature. Jan. 6, 1994;367(6458):69-72.

Subramaniam et al., Aspartic acid 85 in bacteriorhodopsin functions both as proton acceptor and negative counterion to the Schiff base. J Biol Chem. Dec. 25, 1992;267(36):25730-3.

Subramaniam et al., Protonation state of Asp (Glu)-85 regulates the purple-to-blue transition in bacteriorhodopsin mutants Arg-82—Ala and Asp-85—Glu: the blue form is inactive in proton translocation. Proc Natl Acad Sci U S A. Feb. 1990;87(3):1013-7.

Takahashi et al., Light-addressed single-neuron stimulation in dissociated neuronal cultures with sparse expression of ChR2. Biosystems. Feb. 2012;107(2):106-12. doi: 10.1016/j.biosystems.2011.10.002. Epub Oct. 14, 2011.

Tantama et al., Imaging energy status in live cells with a fluorescent biosensor of the intracellular ATP-to-ADP ratio. Nat Commun. 2013;4:2550. doi: 10.1038/ncomms3550.

Tateno et al., The novel ion pump rhodopsins from Haloarcula form a family independent from both the bacteriorhodopsin and archaerhodopsin families/tribes. Arch Biochem Biophys. Nov. 15, 1994;315(1):127-32.

Thevenin et al., A novel photoactivatable cross-linker for the functionally-directed region-specific fluorescent labeling of proteins. Eur J Biochem. Jun. 1, 1992;206(2):471-7.

Tsuda et al., Probing the function of neuronal populations: combining micromirror-based optogenetic photostimulation with voltage-sensitive dye imaging. Neurosci Res. Jan. 2013;75(1):76-81. doi: 10.1016/j.neures.2012.11.006. Epub Dec. 17, 2012.

Venkatachalam et al., Flash memory: photochemical imprinting of neuronal action potentials onto a microbial rhodopsin. J Am Chem Soc. Feb. 12, 2014;136(6):2529-37. doi: 10.1021/ja411338t. Epub Jan. 27, 2014.

Verburg et al., Mitochondrial membrane potential in axons increases with local nerve growth factor or semaphorin signaling. J Neurosci. Aug. 13, 2008;28(33):8306-15.

Vogt et al., Combining membrane potential imaging with L-glutamate or GABA photorelease. PLoS One. 2011;6(10):e24911. doi: 10.1371/journal.pone.0024911. Epub Oct. 11, 2011.

Wachter., The family of GFP-like proteins: structure, function, photophysics and biosensor applications. Introduction and perspective. Photochem Photobiol. Mar.-Apr. 2006;82(2):339-44.

Wang et al., Laser-evoked synaptic transmission in cultured hippocampal neurons expressing channelrhodopsin-2 delivered by adeno-associated virus. J Neurosci Methods. Oct. 15, 2009;183(2):165-75. doi: 10.1016/j.jneumeth.2009.06.024. Epub Jun 26, 2009.

Wang et al., Non-viral gene delivery methods. Curr Pharm Biotechnol. Jan. 2013;14(1):46-60.

Wardill et al., A neuron-based screening platform for optimizing genetically-encoded calcium indicators. PLoS One. Oct. 14, 2013;8(10):e77728. doi: 10.1371/journal.pone.0077728. eCollection 2013.

Waschuk et al., Leptosphaeria rhodopsin: bacteriorhodopsin-like proton pump from a eukaryote. Proc Natl Acad Sci U S A. May 10, 2005;102(19):6879-83. Epub Apr. 28, 2005.

White, Membrane fusion. Science. Nov. 6, 1992;258(5084):917-24.

White, Viral and cellular membrane fusion proteins. Annu Rev Physiol. 1990;52:675-97.

Williams et al., Computational optogenetics: empirically-derived voltage- and light-sensitive channelrhodopsin-2 model. PLoS Comput Biol. 2013;9(9):e1003220. doi: 10.1371/journal.pcbi.1003220. Epub Sep. 12, 2013.

Wu et al., Improved orange and red $Ca^{2+}$ indicators and photophysical considerations for optogenetic applications. ACS Chem Neurosci. Jun. 19, 2013;4(6):963-72. doi: 10.1021/cn400012b. Epub Mar. 19, 2013.

Yan et al., Synthesis and characterization of a photocleavable cross-linker and its application on tunable surface modification and protein photodelivery. Bioconjug Chem. Sep.-Oct. 2004;15(5):1030-6.

Yan et al., Palette of fluorinated voltage-sensitive hemicyanine dyes. Proc Natl Acad Sci U S A. Dec. 11, 2012;109(50):20443-8. doi: 10.1073/pnas.1214850109. Epub Nov. 20, 2012.

Yizhar et al., Optogenetics in neural systems. Neuron. Jul. 14, 2011;71(1):9-34. doi: 10.1016/j.neuron.2011.06.004.

Zhao et al., An expanded palette of genetically encoded $Ca^{2+}$ indicators. Science. Sep. 30, 2011;333(6051):1888-91. doi: 10.1126/science.1208592. Epub Sep. 8, 2011.

Zhao et al., Molecular evolution by staggered extension process (StEP) in vitro recombination. Nat Biotechnol. Mar. 1998;16(3):258-61.

\* cited by examiner

OPTICAL SELECTION OF CELLS

RELATED APPLICATIONS

This application claims priority under 35 U.S.C. § 119(e) to U.S. Provisional Application, U.S. Ser. No. 62/103,844, filed Jan. 15, 2015, which is incorporated herein by reference.

GOVERNMENT SUPPORT

This invention was made with government support under grant numbers N00014-11-1-0549, R01-EB012498-01, and 1-DP2-OD007428 awarded by the Office of Naval Research and the National Institutes of Health. The government has certain rights in the invention.

BACKGROUND

The ability to select a small number of cells from a heterogeneous population is fundamental to many aspects of biological research. Selections form the basis of genetic screens, of protein engineering and directed evolution, and of protocols to produce stably transformed or genome-edited cell lines. In many instances, one would like to select cells on the basis of complex dynamic or morphological features. For example, in a culture of olfactory neurons, one might screen for calcium flux in response to a specific odorant and then wish to select responsive cells for subsequent transcriptional profiling. Or in a culture with single genes knocked down by an siRNA library,[1, 2] one might find cells with unusual shapes, organelle sizes, or metabolic responses; and then wish to select these cells to determine which gene had been knocked down. These types of selections are difficult to perform with existing tools.

Sorting of target cells from a heterogeneous pool is technically difficult when the selection criterion is complex, e.g., a dynamic response, a morphological feature, or a combination of multiple parameters. At present, mammalian cell selections are typically performed either via static fluorescence (e.g., fluorescence activated cell sorter), via survival (e.g. antibiotic resistance), or via serial operations (flow cytometry, laser capture microdissection).

The most common selection technique uses fluorescence-activated cell sorting (FACS),[3] which requires a robust static fluorescence signal. In FACS, cells are suspended in a fine stream of droplets which pass through one or more laser detection points. Cells whose fluorescence falls within user-specified bounds are electrostatically deflected into a collection well.[3] There are several limitations to this method. FACS requires a robust fluorescence signal. Due to the limited observation time per cell (typically about 10 µs) the level of noise is high, and it is not possible to discriminate small changes in fluorescence levels or weak fluorescence signals. FACS probes fluorescence at only a single moment in time. Dynamical quantities, e.g., beat rate, locomotion, subcellular transport, or timecourse of response to a perturbation are not amenable to FACS. FACS also does not provide structural information. Morphological attributes, such as cell shape or subcellular distribution of mitochondria are not amenable to FACS. FACS requires cells to be in suspension. Thus parameters that are disrupted by suspending cells are not a suitable basis for FACS. Some cells such as neurons suffer damage or low viability when suspended in solution.

Laser-capture microdissection (LCM)[4, 5] selects cells or tissue regions one at a time, and so can have limited throughput, and is usually performed on samples that have been chemically fixed. LCM selects cells or tissue regions with a brief and intense pulse of laser light which catapults the selected cells onto a capture membrane.[4, 5] In some variations on LCM, a thermo-adhesive membrane is locally heated by a laser and thereby locally adheres to the cells of interest. The limitations of LCM are: due to its serial nature, LCM can have limited throughput; LCM is usually performed on samples that have been chemically fixed, and so is not readily compatible with dynamical properties of cells, nor with subsequent cell growth; LCM requires expensive and highly specialized instrumentation.

Imaging cytometry[6, 7] typically functions in a flow-through geometry, and so is not compatible with selections of surface-bound cells such as neurons; nor with selections that probe dynamic cellular responses.

Photochemical selection techniques such as spatially patterned photodegradation of the cell culture substrate has been demonstrated as a means for selecting cells from culture.[16, 27] In principle this approach allows for the selection of cells on the basis of complex criteria. Spatially patterned photochemistry is becoming widely applied in cell biology for its ability to induce specific reactions in complex patterns of space and time.[8] Photochemical pre-patterning of cell adhesion molecules enables cell growth in specific morphologies,[9-11] and photopatterned hydrogels are now used to direct cell culture in three dimensions.[12-14] In these applications the pattern is defined prior to plating the cells. For screening purposes one would like to define the adhesion pattern after plating the cells, only retaining cells with a user-specified phenotype. Two recent demonstrations showed photochemical release of cells from a photodegradable surface,[15, 16] but in these protocols the surface had to be specially prepared prior to cell culture. The technique has the following limitations. When cells are in contact, cell-cell bonds can prevent isolation of a single cell simply by disrupting the substrate. The techniques require the cells to be cultured on a specially prepared substrate. Long-term culture on a photodegradable substrate may affect cell viability, is not compatible with imaging modalities that would degrade the substrate, and may not be compatible with some cell culture protocols.

Therefore, there remains a need for systems and methods for cell selection from heterogeneous cell cultures while also preserving cell viability.

SUMMARY OF THE INVENTION

Described herein are two techniques, photostick and photolift, for selecting cells from a cell population based on any static or dynamic property that can be identified or imaged. In photostick, a cell of interest is photochemically cross-linked to surface such as a culture dish, glass side, or chip. In photolift, cells are crosslinked to a surface and to neighboring cells and then a cell of interest is photochemically released from the surface and from neighboring cells.

Generally, both photostick and photolift methods for cell selection combine one or more of the following attributes:
1) High-throughput microscopy and automated feature detection. Recent advances in cameras and computational image processing now enable rapid (<1 s) optical profiling of large numbers (>100,000) of cells. Thus one can identify rare cells with complex features of interest from a heterogeneous population. For example, by using a custom ultra-wide field epi-fluorescence microscope equipped with a digital micromirror device (DMD) to pattern the violet illumination, multiple single cells can be selected in parallel from fields of view containing up to ~4,000 cells.

2) Photochemical targeting. Provided herein are organic molecules (i.e., photochemical crosslinkers and photocleavable crosslinkers) which enable photochemical processing of targeted cells.

3) Patterned illumination. A micromirror-based optical system allows targeted illumination of single cells or subcellular regions within a dense culture. Photochemical processes in the illuminated regions selectively retain (photostick method) or release (photolift method) the targeted cells.

Provided herein are photochemical crosslinkers (used interchangeably with the term "photostick reagents") and photocleavable linkers (used interchangeably with the term "photolift reagents"), which are useful in techniques for selecting cells based on any static or dynamic property that can be identified by microscopy and either human selection or digital image processing. The crosslinkers and methods described herein allow cell viability to be preserved.

In one aspect, provided are photochemical crosslinkers comprising a fluorescent dye linked to a radical generator. Upon exposure to the appropriate wavelength of light, the radical generator generates a radical that reacts with protein functional groups on the surface of the cells in the cell population and on the surface of cells used to coat a surface (e.g., culture dish, glass slide, chip, etc.; the surface can be coated as further described herein). The fluorescent dye is useful for imaging the cells to identify a cell of interest. Also provided is a plurality of cells covalently linked to a surface (e.g., the surface of a tissue culture dish, glass slide, chip, etc.) using a photochemical crosslinker described herein.

In another aspect, provided are methods of selecting cells with a feature of interest comprising the steps of providing a culture of cells in a culture dish; imaging the cells to identify a cell of interest; adding a photochemical crosslinker as described herein to the culture of cells; and illuminating the cell of interest with light, whereby the cell of interest becomes attached to the culture dish.

In another aspect, provided are photocleavable crosslinkers comprising a photocleavable linker linking two electrophilic groups to each other. The electrophilic groups on the crosslinker are used to crosslink cells to a surface and to other neighboring cells. Upon exposure to an appropriate wavelength of light, a cell of interest is photochemically released (i.e., cleavage of photolabile group on the photocleavable crosslinker) from the surface and from neighboring cells. Also provided is a plurality of cells covalently linked to a surface and to contacting neighboring cells using a photocleavable crosslinker described herein.

In yet another aspect, provided are methods of selecting cells with features of interest comprising the steps of providing a culture of cells in a culture dish; attaching the cells to the surface of the culture dish and to their contacting neighbors using a photocleavable crosslinker as described herein; imaging the cells to identify a cell of interest; adding a protease to the culture of cells; and illuminating the cell of interest with light, whereby the cell of interest is released from the culture dish.

In one aspect, provided is a system for imaging cells comprising a plurality of cells crosslinked to extracellular matrix proteins using a photochemical crosslinker or photocleavable crosslinker described herein, an imaging apparatus, an illuminating apparatus, and software for image processing.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N.Y., 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1\text{-}10}$ alkyl (such as unsubstituted $C_{1\text{-}6}$ alkyl, e.g., —$CH_3$ (Me), unsubstituted ethyl (Et), unsubstituted propyl (Pr, e.g., unsubstituted n-propyl (n—Pr), unsubstituted isopropyl (i—Pr)), unsubstituted butyl (Bu, e.g., unsubstituted n-butyl (n—Bu), unsubstituted tert-butyl (tert—Bu or t—Bu), unsubstituted sec-butyl (sec—Bu), unsubstituted isobutyl (i—Bu)). In certain embodiments, the alkyl group is a substituted $C_{1\text{-}10}$ alkyl (such as substituted $C_{1\text{-}6}$ alkyl, e.g., —$CF_3$, Bn).

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$ —$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)_2R^{aa}$, —$OP(=O)_2R^{aa}$, —$P(=O)(R^{aa})_2$, —$OP(=O)(R^{aa})_2$, —$OP(=O)(OR^{cc})_2$, —$P(=O)_2N(R^{bb})_2$, —$OP(=O)_2N(R^{bb})_2$, —$P(=O)(NR^{bb})_2$, —$OP(=O)(NR^{bb})_2$, —$NR^{bb}P(=O)(OR^{cc})_2$, —$NR^{bb}P(=O)(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, $C_{1\text{-}10}$ alkyl, $C_{1\text{-}10}$ perhaloalkyl, $C_{2\text{-}10}$ alkenyl, $C_{2\text{-}10}$ alkynyl, hetero$C_{1\text{-}10}$ alkyl, hetero$C_{2\text{-}10}$ alkenyl, hetero$C_{2\text{-}10}$ alkynyl, $C_{3\text{-}10}$ carbocyclyl, 3-14 membered heterocyclyl, $C_{6\text{-}14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =$NN(R^{bb})_2$, =$NNR^{bb}C(=O)$ $R^{aa}$, =$NNR^{bb}C(=O)OR^{aa}$, =$NNR^{bb}S(=O)_2R^{aa}$, =$NR^{bb}$, or =$NOR^{cc}$;

each instance of $R^{aa}$ is, independently, selected from $C_{1\text{-}10}$ alkyl, $C_{1\text{-}10}$ perhaloalkyl, $C_{2\text{-}10}$ alkenyl, $C_{2\text{-}10}$ alkynyl, hetero$C_{1\text{-}10}$ alkyl, hetero$C_{2\text{-}10}$alkenyl, hetero$C_{2\text{-}10}$alkynyl, $C_{3\text{-}10}$ carbocyclyl, 3-14 membered heterocyclyl, $C_{6\text{-}14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})$ $OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)_2R^{aa}$, —$P(=O)(R^{aa})_2$, —$P(=O)_2N(R^{cc})_2$, —$P(=O)(NR^{cc})_2$, $C_{1\text{-}10}$ alkyl, $C_{1\text{-}10}$ perhaloalkyl, $C_{2\text{-}10}$ alkenyl, $C_{2\text{-}10}$ alkynyl, hetero$C_{1\text{-}10}$alkyl, hetero$C_{2\text{-}10}$alkenyl, hetero$C_{2\text{-}10}$alkynyl, $C_{3\text{-}10}$ carbocyclyl, 3-14 membered heterocyclyl, $C_{6\text{-}14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1\text{-}10}$ alkyl, $C_{1\text{-}10}$ perhaloalkyl, $C_{2\text{-}10}$ alkenyl, $C_{2\text{-}10}$ alkynyl, hetero$C_{1\text{-}10}$ alkyl, hetero$C_{2\text{-}10}$ alkenyl, hetero$C_{2\text{-}10}$ alkynyl, $C_{3\text{-}10}$ carbocyclyl, 3-14 membered heterocyclyl, $C_{6\text{-}14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})$ $R^{ff}$, —SH, —$SR^{ee}$, —$SSR^{ee}$, —$C(=O)R^{ee}$, —$CO_2H$, —$CO_2R^{ee}$, —$OC(=O)R^{ee}$, —$OCO_2R^{ee}$, —$C(=O)N(R^{ff})_2$, —$OC(=O)N(R^{ff})_2$, —$NR^{ff}C(=O)R^{ee}$, —$NR^{ff}CO_2R^{ee}$, —$NR^{ff}C(=O)N(R^{ff})_2$, —$C(=NR^{ff})OR^{ee}$, —$OC(=NR^{ff})$ $R^{ee}$, —$OC(=NR^{ff})OR^{ee}$, —$C(=NR^{ff})N(R^{ff})_2$, —$OC(=NR^{ff})N(R^{ff})_2$, —$NR^{ff}C(=NR^{ff})N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —$S(=O)R^{ee}$, —$Si(R^{ee})_3$, —$OSi(R^{ee})_3$, —$C(=S)N(R^{ff})_2$, —$C(=O)SR^{ee}$, —$C(=S)SR^{ee}$, —$SC(=S)SR^{ee}$, —$P(=O)_2$ $R^{ee}$, —$P(=O)(R^{ee})_2$, —$OP(=O)(R^{ee})_2$, —$OP(=O)$ $(OR^{ee})_2$, $C_{1\text{-}6}$ alkyl, $C_{1\text{-}6}$ perhaloalkyl, $C_{2\text{-}6}$ alkenyl, $C_{2\text{-}6}$ alkynyl, hetero$C_{1\text{-}6}$alkyl, hetero$C_{2\text{-}6}$alkenyl, hetero$C_{2\text{-}6}$alkynyl, $C_{3\text{-}10}$ carbocyclyl, 3-10 membered heterocyclyl, $C_{6\text{-}10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

The term "surface" refers to any non-biological surface such as the surface of a tissue culture dish, a glass slide, or a chip (e.g., cell chip). In certain embodiments, the surface is coated. The surface can be coated with any biological or non-biological material/substrate or molecule that can react with a radical generated from the photochemical crosslinkers used or that can react with the electrophilic groups on the photocleavable crosslinkers. In certain embodiments, the surface is coated with amino acids (natural or non-natural) or analogs. In certain embodiments, the surface is coated with cell adhesion molecules (can be biological or non-biological). For example For example, cell adhesion proteins such as an extracellular matrix protein. Non-limiting examples of such proteins include fibronectin, collagen, laminin, fibrillin, vitronectin, thrombospondins, tenascins, entactins (or nidogens), nephronectin, or fibrinogen, osteopontin, agrin, aggrecan, decorin, F-Spondin, matrix extracellular phosphoglycoprotein (MEPE), nidogen-1, testican, poly-L-lysine, poly-D-lysine, poly-L-orinthine, or a combination thereof.

BRIEF DESCRIPTION OF THE FIGURES

The accompanying drawings are not intended to be drawn to scale. In the Drawings, for purposes of clarity, not every component may be labeled in every drawing.

FIG. 1A shows an exemplary sequence of steps in the photostick method. Photochemical immobilization retains target cells while others are washed away upon mild protease treatment. FIG. 1B shows an exemplary photochemical crosslinker, which contains three functional moieties (fluorescent dye (e.g., Cy-3 or Cy-5), radical generator (e.g., SBED), protein tag (e.g., biotin moiety)). The trifunctional crosslinkers Cy3- and Cy5-SBED (SBED=N-hydroxysuccinimidyl-2-(6-[biotinamido]-2-(p-azido benzamido)-hexanoamido)ethyl-1,3'-dithioproprionate) used for photochemical immobilization with simultaneous fluorescent labeling and biotinylation. The biotin moiety, which may be used for affinity purification or labeling, is optional. FIG. 1C is a schematic of a digital micromirror device (DMD) for patterned violet illumination to activate photochemical crosslinkers.

FIG. 4A is a transmitted light image of MDCK cells. FIG. 4B shows cells exposed to Cy3-SBED (4 μM) and illuminated with two squares of violet light. The cells were then exposed to Cy5-SBED and exposed to a bar of violet light. After development with ACCUTASE®, cells that had been illuminated were preferentially retained. The image shows a composite of transmitted light (grey area), fluorescence of Cy3 (area indicated with dashed arrow), and fluorescence of Cy5 (area indicated with solid arrow) after this protocol. FIG. 4C is a close-up of the overlap of the Cy3- and Cy5-labeled regions, showing absence of intracellular labeling by either dye. FIG. 4D shows a partial low-magnification field of view from a dish of MDCK cells labeled with 2 µM calcein-acetoxymethyl (AM) before applying photostick with 4 µM Cy3-SBED. FIG. 4E shows the same field of view as FIG. 4D after photostick and ACCUTASE® development. Cells in the illuminated region remained, while most others were washed away. FIG. 4F shows a quantification of photostick selectivity and specificity. Cells within the illuminated region were retained with high efficiency (147/149, 98.7%, n=9 experiments; bar 1), and cells in the dark region were removed with high efficiency (99.96%, 21 false positives of ~50,000 cells; bar 2). Scale bar: FIGS. 4A-4B, 50 µm; FIG. 4C, 30 µm; FIGS. 4D-4E, 200 µm.

In FIGS. 5A and 5B, a photostick of a single YFP-expressing MDCK cell, using 4 µM Cy5-SBED, is shown. FIG. 5A is a merged bright field and YFP image prior to photostick. FIG. 5B shows a merged image after a photostick. FIG. 5C depicts the PCR detection of the YFP gene from the cell in FIG. 5B. Lane 1: YFP gene (713 bp) amplified from the cell selected by photostick. Lane 2: PCR amplification of a non-fluorescent cell did not produce a band. Lane 3: PCR of purified YFP gene. FIGS. 5D-5G show a photostick of three YFP-expressing MDCK cells, using 4 µM Cy5-SBED, from a mixed culture of cells expressing either YFP or mOrange. FIG. 5D is a merged image before photostick. FIG. 5E is a zoomed-in image from FIG. 5D. FIG. 5F shows a merged image after photostick. FIG. 5G is a zoomed-in image from FIG. 5F. FIG. 5H shows PCR detection of YFP in cells selected by photostick from FIG. 5G. Lane 1: YFP (1017 bp) amplified with consensus primers for YFP and mOrange (Con-primers). Lane 2: PCR amplification with mOrange specific primers (mO2 primers). No mOrange gene was detected. Lane 3: PCR of purified YFP gene with Con-primers. Lane 4: PCR of purified mOrange gene with Con-primers. Scale bar: FIGS. 5A-5B: 30 µm; FIGS. 5D, 5F: 500 µm; FIGS. 5E, 5G: 100 µm.

FIG. 6A is an image of GFP fluorescence in neurons expressing the Optopatch construct prior to cell selection via photostick. FIG. 6B is a GFP image after photostick. FIG. 6D shows the single-cell PCR detection of a partial Optopatch gene (745 bp) in a single neuron selected by photostick. Lane 1: Optopatch gene (745 bp) amplified from a single cell selected by photostick. Lane 2: PCR negative control without cell lysate. Lane 3: PCR of purified Optopatch gene.

FIG. 7A shows the cells prior to the photolift. Dashed circle indicates the target cell. FIG. 7B shows that the target cell has been selectively illuminated with violet light for 1-2 min. FIG. 7C shows that the target cell has been aspirated through the glass pipette. FIG. 7D is the image post-photolift and aspiration. The target cell is removed from the culture dish (dashed circle).

FIGS. 8A-8D show photosticking MDCK cells with FNPA (4-Fluoro-3-nitrophenyl azide). In FIG. 8A, FNPA (4 µM) was added to MDCK cells (FIG. 8B) followed by projecting a square pattern of 407 nm light via digital micromirror device (DMD) onto cells for 15 min (825 J/cm$^2$). Cells were then rinsed three times with DPBS (FIG. 8C) followed by addition of ACCUTASE® at 37° C. for 3 min. A rectangular pattern of MDCK cells can be observed after ACCUTASE® development (FIG. 8D). Scale bar=100 µm.

FIG. 9E). Cy3-SBED at 0.5 µM, 1 µM, 4 µM, 5 µM, and 20 µM was added to MDCK cells, followed by projecting a square pattern of 407 nm light (825 J/cm$^2$) via DMD onto the cells. Cells were then rinsed three times with DPBS followed by addition of ACCUTASE® at 37° C. for 3 min. Cy3-SBED concentration above 4 µM yielded good Photostick efficiency. FIGS. 9A-9D show representative data. FIG. 9A shows merged fluorescence and bright field images before ACCUTASE® treatment with 0.5 µM Cy3-SBED. FIG. 9B shows the same sample as FIG. 9A after ACCUTASE® treatment. FIGS. 9C and 9D are the same as FIGS. 9A and 9B but with 4 µM Cy3-SBED. Scale bar=100 µm.

FIG. 10E). 4 µM of Cy3-SBED was added to MDCK cells followed by projecting a square pattern of 407 nm light onto the cells with a DMD. After treatment with ACCUTASE® (37° C. for 3 min), the efficiency was calculated as the number of cells remaining divided by the number of cells illuminated. Illumination light doses above 550 J/cm$^2$ yielded high photosticking efficiencies. FIGS. 10A-10D show representative data. FIG. 10A shows merged fluorescence and bright field images before ACCUTASE® treatment with illumination dose of 275 J/cm$^2$. FIG. 10B shows the same sample as FIG. 10A after ACCUTASE® treatment. FIGS. 10C and 10D are the same as FIGS. 10A and 10B but with illumination dose of 825 J/cm$^2$. Scale bar=50 µm.

FIG. 11A shows a bright-field image after exposure but before ACCUTASE® treatment. FIG. 11B shows combined fluorescence and bright-field images after treatment with ACCUTASE® (3 min, 37° C.). Cells were then incubated at 37° C., 5% CO$_2$ for 16 hours before LIVE/DEAD viability staining (Life Technologies, Part Number: L-3224). FIG. 11C shows live cells stained with green-fluorescent Calcein-AM to indicate intracellular esterase activity. FIG. 11D shows dead cells stained with red-fluorescent ethidium homodimer-1 (EthD-1) indicating loss of plasma membrane integrity. The survival rate was 98%. Scale bar=100 µm.

FIG. 12A is a bright-field image merged with Cy3 image after 407 nm illumination. FIG. 12B is a bright-field image merged with Cy3 image after ACCUTASE® development. FIGS. 12C-12E show bright-field images of MDCK cells after 1, 2 and 4 days, respectively, showing cell growth and migration. FIG. 12F shows the cell doubling time post-photostick is 34 hrs. Scale bar=200 µm.

J/cm$^2$) was selectively projected onto a small cluster of YFP-MDCK cells using a pair of galvo mirrors. FIG. 13A shows the combined bright-field and YFP fluorescence image after 407 nm illumination. Illuminating pattern indicated with an outlined border (shown with white arrow). FIG. 13B shows the combined bright-field and YFP fluorescence image after ACCUTASE® treatment. Scale bar=30 µm.

DETAILED DESCRIPTION OF THE INVENTION

Figure 1A:
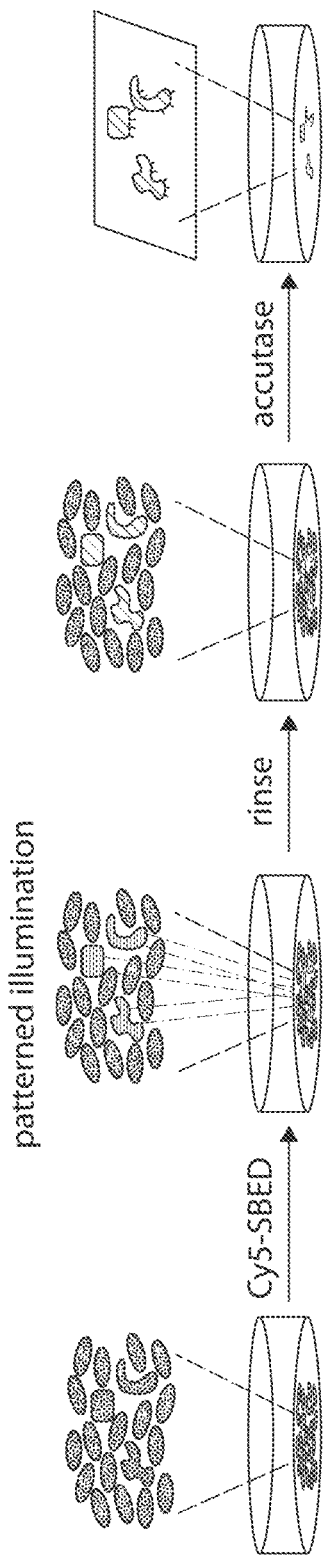
FIGS. 1A-1C depict components of the photostick protocol.

The present invention is based, at least in part, on the development of systems, apparatuses, compositions, reagents, and methods for the selection of cells using photochemical crosslinkers (used interchangeably with the term "photostick reagents") and photocleavable crosslinkers (used interchangeably with the term "photolift reagents") further described herein. The methods and crosslinkers provided herein can be used to select and/or isolate one or more cells of interest from a culture of cells (e.g., tissue culture substrate). The cell section methods provided herein allow cell viability to be preserved. The methods described herein are based on any static or dynamic property of the cell that can be imaged or determined (e.g., using microscopy).

Photochemical radical initiators have been used in macroscopic tissue bonding applications[17] and found to produce minimal toxicity.[18] The first type of crosslinker provided herein are photochemical crosslinkers (photostick reagents) which comprise a radical generator and a fluorescent dye. The photochemical crosslinkers are used in a technique called "photostick" which uses a photochemical crosslinker and illumination (e.g., pattern illumination using, for example, a digital micromirror array) to generate radicals for immobilizing one or more selected cells of interest on a surface (e.g., culture dish). One or more cells of interest remain immobilized on the culture dish. Other cells can optionally be washed away upon treatment with an enzyme (e.g., mild protease treatment). The photochemical crosslinker also comprises a fluorescent dye useful for labeling the selected cells and optionally a tag (e.g., biotin) for later identification of the cell. Other embodiments of the photochemical crosslinkers are more fully described herein.

The second type of crosslinker provided herein is a photocleavable crosslinker which comprise a photocleavable linker linking two electrophilic groups to each other. The photocleavable crosslinkers (photolift reagents) are used in a technique called "photolift" which uses photocleavable crosslinkers and illumination (e.g., patterned illumination) to photochemically release one or more selected cells of interest from a culture dish while other cells remain behind. In certain embodiments, the released cells are removed from the culture dish (e.g., using aspiration). The cells can then be used for further characterization. In certain embodiments, the cells are subject to subsequent RNA analysis and/or DNA sequencing. Other embodiments of the photocleavable crosslinkers are more fully described herein.

In both the photostick and photolift methods, the cell viability is preserved. In certain embodiments, cell viability is preserved by more than about 50%, 60%, 70%, 80%, 90%, 95%, 98%, or 99%. In certain embodiments, the photostick and photolift methods permits genetic profiling of selected cells. The cells are isolated and then subject to biochemical analyses such as DNA analysis or RNA analysis. In certain embodiments, the photostick or photolift method is performed with complex functional selection criteria such as neuronal firing patterns (i.e., the cells are selected based on a particular neuronal firing pattern).

Both photostick and photolift methods involve a cell culture and are applicable to any two-dimensional surface such as a culture dish/surface, glass slide, chip, etc. In certain embodiments, modifications are not made to standard cell culture protocols in order to use the cell selection methods herein. In certain embodiments, modifications are made to standard cell culture protocols. The methods are used in heterogeneous cell cultures, where a subset of the cells manifests a feature that can be observed or imaged.

Both photostick and photolift methods use imaging to identify one or more cells of interest. In certain embodimentents, microscopic imaging is used for cell identification. In certain embodiments, one or more optical microscopies are used to evaluate features of interest for a large number of cells. In certain embodiments, the number of cells is between about 100 to about 100,000 cells per field-of-view. In certain embodiments, the number of cells is between about 100 to about 50,000 cells per field-of-view. In certain embodiments, the number of cells is between about 50,000 to about 100,000 cells per field-of-view. In certain embodiments, the number of cells is between about 50-100 cells per field-of-view. In certain embodiments, the number of cells is between about 100,000 to about 500,000 cells per field-of-view. In certain embodiments, manual image processing routines are used to identify one or more the cells of interest. In certain embodiments, automated image processing routines are used to identify one or more the cells of interest. Various manual and automated image processing routines are known in the art.

Both photostick and photolift methods involve adding a crosslinker reagent (photochemical crosslinker for photostick or photocleavable crosslinker for photolift) described herein to the culture of cells.

Both photostick and photolift methods involve illuminating one or more cells of interest with light, as further described herein. In the photostick method, the light used for illumination generates a radical from the photochemical crosslinker, which causes one or more cells of interest to be attached to a surface (e.g., the surface of a tissue culture dish, glass slide, or a chip; the surface can be coated as further described herein). In the photolift method, the light used for illumination causes the labile portion of the photocleavable crosslinker to cleave one or more cells of interest are released from the surface (e.g., the surface of a tissue culture dish, glass slide, or a chip; the surface can be coated as further described herein). In the photolift method, prior to one or more cells of interest being released from the surface, the surface is washed. For example, media or buffer can be used. In certain embodiments, a protease is used in the washing step. In certain embodiments of the photolift method, prior to one or more cells of interest being released, native cell-cell and cell-surface interactions are cleaved adding an appropriate enzyme (e.g., a protease) to the cells on the surface. In certain embodiments, illumination with light is targeted to one or more cells of interest for a particular time. In certain embodiments, the light used for illumination is violet light (i.e., about 400 nm to about 440 nm). In certain embodiments, the light used for illumination is near-ultraviolet light (i.e., about 300 nm to about 400 nm). In certain embodiments, the light used for illumination is blue light (i.e., about 440 nm to about 500 nm). In certain embodiments, the light used for illumination is about 300 nm to about 360 nm. In certain embodiments, the light used for illumination is about 360 nm to about 400 nm. In certain embodiments, the light used for illumination is about 400 nm to about 420 nm. In certain embodiments, the light used for illumination is about 420 nm to about 440 nm. In certain embodiments, the light used for illumination is about 440 nm to about 500 nm. As discussed above, the wavelength of light used is any wavelength appropriate for generating radicals from the photochemical crosslinker or for cleaving the photocleavable crosslinker. It is also understood that the wavelength and intensity of light used should not cause damage to the cells.

Both photostick and photolift methods optionally involve further growth and/or characterization of cells of interest. In certain embodiments, the cells of interests are expanded as a clonal population. In certain embodiments, the cells of interests are characterized via sequencing, microscopy, proteomics, and/or biochemical analyses. Non-limiting examples of biochemical analyses include gene-chip analysis, RNA analysis, DNA sequence of a portion of the genome or whole genome.

Photochemical Crosslinker (Photostick Reagent)

Provided herein are photochemical crosslinkers comprising a fluorescent dye and a radical generator. The photochemical crosslinker (photostick reagent) typically does not penetrate the cell membrane. The photochemical crosslinker should also generate free radicals upon illumination with the appropriate light (e.g., visible light (e.g., violet light, blue light) or ultra-violet light (e.g., near-ultraviolet light)).

The photochemical crosslinker is capable of cross-linking a cell to a surface. Upon illumination of the photochemical crosslinker with an appropriate wavelength of light, the radical that is generated reacts with protein functional groups on the surface of the cells in the cell population and on the surface of cells used to coat a surface (e.g., culture dish, glass slide, chip, etc.). In certain embodiments, the cell being crosslinked is a living cell. In certain embodiments, the surface is the surface of a tissue culture dish. In certain embodiments, the surface is the surface of glass side. In certain embodiments, the surface is the surface of a chip. In certain embodiments, the surface is coated. The surface can be coated with any biological or non-biological material or molecule that can react with a radical generated from the photochemical crosslinkers used or that can react with the electrophilic groups on the photocleavable crosslinkers.

In certain embodiments, the fluorescent dye is excited by a wavelength of light that does not overlap with the wavelength of light used for activating the radical generator. The fluorescent dye can be excited with light having a wavelength of about 500 nm to about 750 nm. In certain embodiments, the fluorescent dye is excited with green-light (i.e., about 500 nm to about 565 nm). In certain embodiments, the fluorescent dye is excited with yellow-light (i.e., about 560 nm to about 585 nm). In certain embodiments, the fluorescent dye is excited with orange-light (i.e., about 580 nm to about 620 nm). In certain embodiments, the fluorescent dye is excited with red-light (i.e., about 600 nm to about 750 nm). In certain embodiments, the fluorescent dye is excited with red-light (i.e., about 500 nm to about 565 nm). It is understood in the art that, since light is a spectrum, there will be overlap in wavelengths found between the adjacent colors in the spectrum.

Any fluorescent dye known in the art may be used in the present invention. In certain embodiments, the fluorescent dye is water soluble. In certain embodiments, the fluorescent dye is hydrophilic. In certain embodiments, the fluorescent dye does not penetrate the cell membrane. The fluorescent dye may not penetrate the cell due to its hydrophilicity. The photochemical crosslinker reagent can use any fluorescent dye which include reactive groups for conjugating the fluorescent dye to the radical generator. In certain embodiments, the fluorescent dye useful in the present invention comprises an amine (e.g., a primary or secondary amine) as the reactive reactive group, which can react with an electrophile such as a succinimide ester on the radical generator. Exemplary dyes useful in the present invention include, but are not limited to, cyanine dyes, Alexa Fluor dyes, ATTO dyes, fluorescein, and rhodamine dyes. Non-limiting examples of Alexa Fluor dyes include, but are not limited to, Alexa Fluor 350, Alexa Fluor 405, Alexa Fluor 430, Alexa Fluor 488, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, and Alexa Fluor 790. Non-limiting examples of ATTO dyes include, but are not limited to, ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740. Non-limiting examples of cyanine and related dyes include, but are not limited to, Cy3, Cy5, Cy7, Cy3.5, Cy5.5, Cy3b, Quasar 570, Quasar 670, and Quasar 705. Non-limiting examples of fluorescein, rhodamines, and other dyes include, but are not limited to, fluorescein (FAM), TET, JOE, VIC, HEX, NED, PET, ROX, TAMRA, Texas Red, Yakima Yellow, Rhodamine B, Lissamine Rhodamine B, Rhodamine 6G, Rhodamine 123, TMR, TRITC, FITC, Napthofluorescein, Carboxyrhodamine 6G, Sulforhodamine 101, Rhodamine Red, ROX, Oregon Green 488, Oregon Green 514, Rhodamine Green, Rhodamine Green-X, Eosin, and Zenon. Additional non-limiting examples of dyes include, but are not limited to, DyLight Fluor dyes, such as DyLight 360, DyLight 405, DyLight 488, DyLight 550, DyLight 594, DyLight 633, DyLight650, DyLight 680, DyLight 755, and DyLight 800; BODIPY dyes, such as BODIPY 493/501, BODIPY FL-X, BODIPY FL, BODIPY R6G, BODIPY 530/550, BODIPY TMR, BODIPY 558/568, BODIPY 564/570, BODIPY 576/589, BODIPY 581/591, BODIPY TR, BODIPY 630/650, BODIPY 650/665, and Chromis 500N; and CAL Fluor dyes, such as CAL Fluor Green 510, CAL Fluor Gold 540, CAL Fluor Orange 560, CAL Fluor Red 590, CAL Fluor Red 610, CAL Fluor Red 615, and CAL Fluor Red 635.

The radical generation is activated by an appropriate wavelength of light, which generates a free radical, that attaches to a molecule on a surface as described herein or to the surface of a cell. In certain embodiments, the radical generator is activated by violet light (i.e., about 400 nm to about 440 nm). In certain embodiments, the radical generator is activated by near-ultraviolet light (i.e., about 300 nm to about 400 nm). In certain embodiments, the radical generator is activated by blue light (i.e., about 440 nm to about 500 nm). In certain embodiments, the radical generator is activated by light having a wavelength of about 300 nm to about 360 nm. In certain embodiments, the radical generator is activated by light having a wavelength of about 360 nm to about 400 nm. In certain embodiments, the radical generator is activated by light having a wavelength of about 400 nm to about 420 nm. In certain embodiments, the radical generator is activated by light having a wavelength of about 420 nm to about 440 nm. In certain embodiments, the radical generator is activated by light having a wavelength of about 440 nm to about 500 nm.

Any radical generator known in the art may be used in the present invention. In certain embodiments, the radical generator is cell-impermeant. Preferably the radical generator can be used to generate a free radical without substantially harming a living cell. In certain embodiments, there is less than about a 1%, 2%, 5%, 10%, 20%, 25%, 30%, or 50% loss of viabile cells as determined by cell viability assays known in the art. In certain embodiments, the radical generator is derived from a nitrene radical generator or a carbene radical generator. In certain embodiments, the nitrene radical generator is sulfo-N-hydroxysuccinimidyl-2-(6-[biotinamido]-2-(p-azido benzamido)-hexanoamido) ethyl-1,3'-dithiopropionate (Sulfo-SBED); 4-fluoro-3-nitrophenyl azide; succinimidyl 6-(4'-azido-2'-nitrophenylamino)hexanoate (SANPAH); sulfosuccinimidyl 6-(4'-azido-2'-nitrophenylamino)hexanoate (sulfo-SANPAH); N-hydroxysuccinimidyl-4-azidosalicylic acid (NHS-ASA); sulfosuccinimidyl-2-(p-azidosalicylamido) ethyl-1,3'-dithiopropionate (SASD); N-hydroxysuccinimidyl-4-azidobenzoate (HSAB); N-5-azido-2-nitrobenzoyloxysuccinimide (ANB-NOS); sulfosuccinimidyl-2-(m-azido-o-nitrobenzamido)-ethyl-1,3'-dithiopropionate (SAND); N-succinimidyl-(4-azidophenyl)1,3'-dithiopropionate (SADP); sulfosuccinimidyl 4-(p-azidophenyl)butyrate (Sulfo-SAPB); sulfosuccinimidyl 2-(7-azido-4-methylcoumarin-3-acetamide)ethyl-1,3'-dithiopropionate (SAED); sulfo-SAMCA, sulfosuccinimidyl 7-azido-4-methylcoumain-3-acetate; 1-(p-azidosalicylamido)-4-(iodoacetamido) butane (ASIB); N-[4-(p-azidosalicylamido)butyl]-3'-(2'-pyridyldithio) (APDP).

In certain embodiments, the carbene radical generator is derived from Succinimidyl 4,4'-azipentanoate (NHS-diazirine); sulfo-NHS-diazirine; succinimidyl 6-(4,4'-azipentanamido)hexanoate (NHS-LC-Diazirine); sulfo-NHS-LC-Diazirine; succinimidyl 2-([4,4'-azipentanamido]ethyl)-1,3'-dithiopropionate (NHS-SS-Diazirine); or sulfo-NHS-SS-Diazirine.

In certain embodiments, the photochemical crosslinker is derived from radical generators such as a nitrophenyl azide derivative. In certain embodiments, photochemical crosslinker is derived from sulfo-SBED ((Sulfo-N-hydroxysuccinimidyl-2-(6-[biotinamido]-2-(p-azido benzamido)-hexanoamido)ethyl-1,3'-dithioprorionate)) conjugated to a fluorescent dye. In certain embodiments, the photochemical crosslinker is derived from 4-fluoro-3-nitrophenyl azide (FNPA). In certain embodiments, the fluorescent dye is an aminated fluorescent dye. In certain embodiments, the fluorescent dye is Cy3. In certain embodiments, the fluorescent dye is Cy5. In certain embodiments, the photochemical crosslinker is Cy3-SBED. In certain embodiments, the photochemical crosslinker is Cy5-SBED. FIG. 1B shows the chemical structure of the exemplary photochemical crosslinkers, Cy3-SBED and Cy5-SBED.

In certain embodiments, the photochemical crosslinker is derived from radical generators such as Tris(2,2'-bipyridyl) dichlororuthenium(II) (Ru(bpy)$_3$) or rose-bengal.

In certain embodiments, the photochemical crosslinker further comprises a tag. Such tags are useful for affinity purification or for downstream labeling or identification with other molecules (e.g., biotin moiety labeled with streptavidin). In certain embodiments, the tag is a peptide or protein tag. In certain embodiments, the tag comprises a biotin moiety. Additional exemplary tags include, but are not limited to, a BCCP tag, a myc-tag, a calmodulin-tag, a FLAG-tag, a His-tag, a Myc-tag, a V5-tag, a VSV-tag, a HA-tag, a maltose binding protein-tag, a nus-tag, a glutathione-S-transferase-tag, a green fluorescent protein-tag, a thioredoxin-tag, a S-tag, a Softag 1, a Softag 3, a strep-tag, a biotin ligase tag, a FlAsH tag, a V5 tag, or a SBP-tag. In certain embodiments, the photochemical crosslinker does not include a tag.

In embodiments where the photochemical crosslinker is a nitrophenyl azide derivative, the nitrophenyl azide dissociates and produces N$_2$ and a nitrene radical[6-8] upon illumination of a cell of interest with the appropriate light (e.g., violet light). The nitrene radical reacts with a functional group of a protein via a sequential abstraction-recombination mechanism.[9, 10] Radical formation on both cell-adhesion proteins (e.g., extracellular matrix proteins, for example, fibronectin) and cellular surface proteins leads to covalent cross-linking of cells to the culture dish surface. Thus the illuminated cell of interest becomes covalently bound to the cell-adhesion protein substrate and labeled with a fluorescent dye (e.g., Cy3 or Cy5). In certain embodiments, the illuminated cell of interest is labeled with a tag such as a biotin functional group linked to the photochemical crosslinker.

In certain embodiments, the fluorescent dye and the radical generator do not contain a linker between the two moieties. In certain embodiments, the fluorescent dye and the radical generator comprise a linker between the two moieties. Any appropriate linker can be used to associate the fluorescent dye with the radical generator. Many techniques and linkers are known in the art for associating chemical moieties (e.g., click chemicals, nucleophile-electrophile pairs; see, for example, Brunner, *New photolabeling and cross-linking methods*, Annu Rev Biochem (1993) 62:483-514); Kluger, et al., *Chemical cross-linking and protein-protein interactions—A review with illustrative protocols*. Bioorg Chem (2004) 32:451-472; Hein et al., *Click Chemistry, a Powerful Tool for Pharmaceutical Sciences*, Pharmaceutical research (2008) 25(10):2216-2230). The linker can be any substituted or unsubstituted C$_{1-50}$ alkylene chain, optionally wherein one or more chain atoms of the alkylene chain are independently replaced with —O—, —S—, —NR—, or —C(=O)—, wherein R is independently hydrogen, or substituted or unsubstituted C$_{1-6}$ alkyl. In certain embodiments, the linker is a substituted or unsubstituted C$_{1-30}$ alkylene chain, optionally wherein one or more chain atoms of the alkylene chain are independently replaced with —O—, —S—, —NR—, or —C(=O)—, wherein R is independently hydrogen, or substituted or unsubstituted C$_{1-6}$ alkyl.

Also provided herein are plurality of cells covalently linked to a surface using a photochemical crosslinker described herein and in any of the foregoing embodiments. The methods herein are useful for any type of cells.

The cells can be eukaryotic and prokaryotic cells. Eukaryotic cells include cells of non-mammalian invertebrates, such as yeast, plants, and nematodes, as well as non-mammalian vertebrates, such as fish and birds. The cells also include mammalian cells, including human cells. The cells also include immortalized cell lines such as HEK, HeLa, CHO, 3T3, which may be particularly useful in applications of the methods for drug screens. The cells also include stem cells, pluripotent cells, progenotir cells, and induced pluripotent cells. Differentiated cells including cells differentiated from the stem cells, pluripotent cells and progenitor cells are included as well. Non-limited examples of cells include neurons, skeletal myocytes, cardiac cells, glial cells, pancreatic beta cells, endothelial cells. the cell can be of any cell type including, but not limited to, epithelial, endothelial, neuronal, adipose, cardiac, skeletal muscle, fibroblast, immune cells, hepatic, splenic, lung, circulating blood cells, reproductive cells, gastrointestinal, renal, bone marrow, and pancreatic cells. The cell can be a cell line, a stem cell, or a primary cell isolated from any tissue including, but not limited to, brain, liver, lung, gut, stomach, fat, muscle, testes, uterus, ovary, skin, spleen, endocrine organ and bone, etc. Where the cell is maintained under in vitro conditions, conventional tissue culture conditions and methods can be used, and are known to those of skill in the art. Isolation and culture methods for various cells are well within the knowledge of one skilled in the art. The cell can be a prokaryotic or eukaryotic cell. In certain embodiments, the cell is a mammalian cell. In certain embodiments, the cell is a human cell. In certain embodiments, the cell is a neuron or other cell of the brain. In certain embodiments, the cell is a cardiomyocyte. In certain embodiments, the cell is cardiomyocyte that has been differentiated from an induced pluripotent cell.

Photostick Method: Method of Selecting Cells Using Photochemical Crosslinkers

In the photostick method, a cell of interest is photochemically crosslinked to a surface such as a culture dish, glass side, or chip. Provided herein are methods of selecting cells with a feature of interest comprising: a) providing a culture of cells in a culture dish; b) imaging the cells to identify a cell of interest; c) adding a photochemical crosslinker as described herein to the culture of cells; and d) illuminating the cell of interest with light, whereby the cell of interest becomes attached to the culture dish. In certain embodiments, the method further comprises washing away cells that are not attached to the culture dish through the crosslinker. In certain embodiments, the step of washing away cells comprises incubating the culture of cells with an enzyme. In certain embodiments, the enzyme is a proteolytic enzyme. In certain embodiments, the enzyme is ACCUTASE®. ACCUTASE® is an enzyme of marine origin with proteolytic and collagenolytic activity for the detachment of primary and stem cell lines and tissues from Innovative Cell Technologies. In certain embodiments, the enzyme is trypsin. Additional examples of agents that can be used to detach and wash away cells include, but are not limited to, collagenase, dispase, and papain. Agents used to detach and wash away cells are known in the art.

In certain embodiments, the method further comprises isolating the cell of interest from the culture dish. In certain embodiments, the method further comprises continuing to grow the cell of interest. In certain embodiments, the method further comprises fixing the cell of interest to the surface. In certain embodiments, the method further comprises removing the cell of interest from the surface. In certain embodiments, the cell of interest is subjected further biological characterization. For example, DNA sequencing, RNA sequencing, biochemical profiling, or proteomic analysis.

In certain embodiments, the culture dish is coated with cell adhesion proteins. In certain embodiments, the cell adhesion protein is an extracellular matrix protein. In certain embodiments, the extracellular matrix protein is fibronectin, collagen, laminin, fibrillin, vitronectin, thrombospondins, tenascins, entactins, nephronectin, fibrinogen, osteopontin, agrin, aggrecan, decorin, F-Spondin, matrix extracellular phosphoglycoprotein (MEPE), nidogen-1, testican, poly-L-lysine, poly-D-lysine, poly-L-orinthine, or a combination thereof. Collagen includes collagen I, IV, native collagen, and denatured collagen (gelatin). In certain embodiments, the extracellular matrix protein is fibronectin.

In certain embodiments, the step of imaging comprises imaging the cell with a wide-field optical system comprising an objective; a means of illumination; and a camera. In certain embodiments, the means of illumination is fluorescent illumination. In certain embodiments, the means of illumination utilizes transmitted light. In certain embodiments, the step of imaging is performed with a high-speed camera. High-speed imaging can be useful for detecting, for example, neuronal action potentials. In certain embodiments, the step of imaging is performed over an extended period of time (long intervals) to detect, for example, changes in circadian period or cell growth. In certain embodiments, the step of imaging is performed using epifluorescensce microscopy, confocal microscopy, differential interference contrast microscopy, phase contrast microscopy, or Raman microscopy.

In certain embodiments, the step of illuminating the cell of interest comprises illuminating the cell with light having a wavelength of about 300 nm to about 360 nm. In certain embodiments, the step of illuminating the cell of interest comprises illuminating the cell with light having a wavelength of about 360 nm to about 440 nm. In certain embodiments, the step of illuminating the cell of interest comprises illuminating the cell with light having a wavelength of about 440 nm to about 500 nm. In certain embodiments, the step of illuminating the cell of interest comprises using patterned illumination. In certain embodiments, the patterned illumination is performed with a digital micromirror device (DMD), galvanometer mirror, acousto-optical beam deflector, or spatial light modulator (SLM).

The method provided below is an example of how the photostick method can be performed.

Cells are cultured on a surface such as a glass-bottom dish coated with cell adhesion molecules such as proteins. For example, the cell adhesion protein is an extracellular matrix protein such as fibronectin. Cell type and cell culture protocol are selected so that a subset of the cells has an attribute of interest, and this attribute is discernable using various methods such as a microscope. The cells should not pile on top of each other.

The cells are imaged, using any appropriate cell visualization method, to identify those with the feature of interest. The protocol is agnostic to the imaging modality and the modality best suited to the feature of interest should be selected. In certain embodiments, cells are imaged in a custom wide-field optical system comprising a 2× objective with a numerical aperture of 0.5, and fluorescence illumination (for example at 488, 532, and 640 nm, depending on the fluorescent dye being used in the crosslinker). A high-speed scientific CMOS (sCMOS) camera captures images of a wide field of view (4 mm×4 mm) with high spatial (3.25 µm) and high temporal (10 ms) resolutions.

Microscope images are then processed to identify cells of interest. The protocol is agnostic to the method of cell identification. In certain embodiments, fluorescence images acquired at two or more times are compared relative to each other to identify cells that exhibited a user-defined temporal pattern of fluorescence.

A photochemical crosslinker is then added to the culture medium. For example, Cy3-SBED is added to the culture medium to a final concentration of 4 µM for MDCK cells, or 15 µM for neurons. In certain embodiments, this crosslinker concentration is adjusted between 0.4 µM and 40 µM for different cell types.

Targeted cells are then illuminated at an appropriate wavelength of light. For Cy3-SBED, cells are illuminated with violet light (e.g., 407 nm wavelength) at a dose of 825 $J/cm^2$ for MDCK cells (see FIG. 2), or 2200 $J/cm^2$ for neurons. The illumination typically restricted to the targeted cells. In certain embodiments, the light is patterned by a digital micromirror device (DMD) positioned in an image plane of the microscope. The DMD is re-imaged onto the sample, creating the specified pattern on the sample.

In certain embodiments, the un-targeted cells or cells not photostuck are subsequently washed away. For example, the dish is incubated with a proteolytic enzyme such as ACCUTASE® at 3 min, 37° C. This treatment removes the un-desired cells, while leaving the desired ones.

In certain embodiments, the selected cells are further processed. For example, if further growth is desired, the cells may simply be left on the dish and maintained in culture medium in the incubator. Alternatively, the cells may be fixed and subjected to biochemical assays such as immunocytochemistry. Alternatively, the cells may be removed from the dish via a stronger protease treatment (typically trypsin) and then subject to clonal expansion, DNA sequencing, RNA sequencing, or proteomic analysis.

It is understood that other variations of the above general methods are possible and are within the scope of the inventions described herein.

Photocleavable Crosslinker (Photolift Reagent)

Provided herein are photocleavable crosslinkers comprising a photocleavable linker moiety linking two electrophilic groups to each other. In culture, cells maintain adhesive contacts to substrates (e.g., the cell-adhesion protein substrates) and to each other. Releasing a cell from the substrate (e.g., via a photodegradable substrate) does not guarantee detachment of the single cell, unless the cell has no neighboring cells. The photocleavable crosslinkers provided herein enable optically targeted scission of cell-cell and cell-substrate bonds. The electrophilic groups (e.g., N-hydroxysuccinimide esters) of the photocleavable crosslinkers react with primary amines on the cell surfaces and the substrate. The photocleavable crosslinkers link cells to each other and to the substrate. These photocleavable crosslinkers are resistant to protease (e.g., trypsin) treatment, but labile to light such as blue, violet, or near-UV light.

In certain embodiments, the photocleavable linker moiety comprises a 2-nitrobenzyl moiety. In certain embodiments, the 2-nitrobenzyl moiety is conjugated to one or both of the electrophilic groups using any appropriate spacing group. In certain embodiments, such spacing group is a substituted or unsubstituted $C_{1-30}$ alkylene chain, optionally wherein one or more chain atoms of the alkylene chain are independently replaced with —O—, —S—, —NR—, or —C(=O)—, wherein R is independently hydrogen, or substituted or unsubstituted $C_{1-6}$ alkyl. In certain embodiments, the spacing group is a substituted or unsubstituted $C_{1-20}$ alkylene chain, optionally wherein one or more chain atoms of the alkylene chain are independently replaced with —O—, —S—, —NR—, or —C(=O)—, wherein R is independently hydrogen, or substituted or unsubstituted $C_{1-6}$ alkyl. In certain embodiments, the spacing group comprises two to five polyethylene glycol units.

In certain embodiments, at least one of the electrophilic groups is a succinimide ester. In certain embodiments, both of the electrophilic groups is a succinimide ester. In certain embodiments, at least one of the electrophilic groups is a N-hydroxysuccinimide ester. In certain embodiments, at least one of the electrophilic groups is fluorophenyl ester. In certain embodiments, at least one of the electrophilic groups is a pentafluorophenyl (PFP) ester or tetrafluorophenyl (TFP) ester. In certain embodiments, at least one of the electrophilic groups is an aldehyde, isothiocyanate, isocyanate, sulfonyl chloride, epoxide, carbonate, aryl halide (e.g., fluorobenzene derivative), imidoester, carbodiimide, or maleimide.

Figure 2:
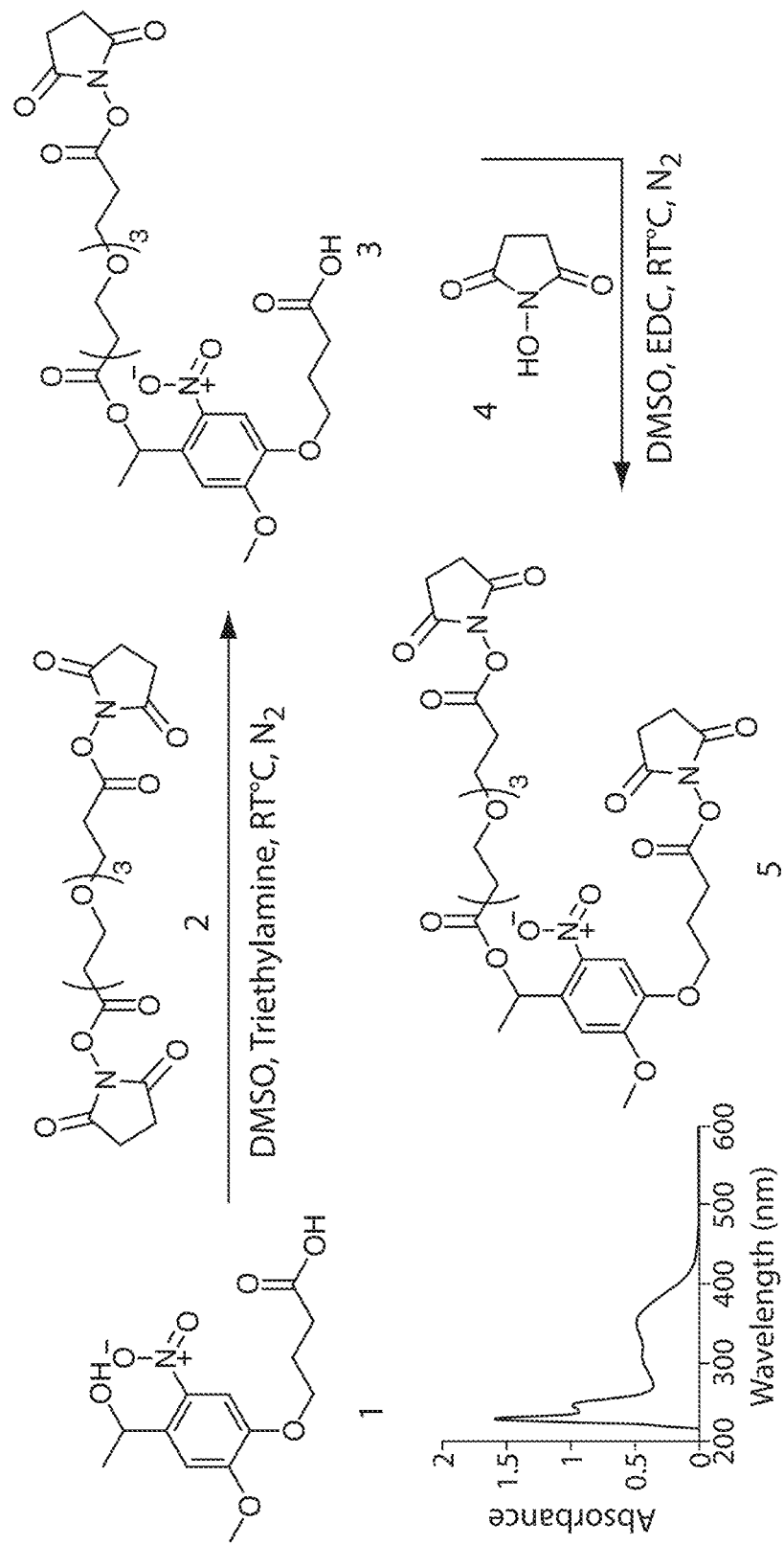
FIG. 2 depicts a scheme for the synthesis of bis-N-hydroxyl succinimide, a photocleavable compound (bis-NHS-PC) useful in the photolift method. In the bottom left panel, the absorption spectrum of bis-NHS-PC is shown.

In certain embodiments, the electrophilic group is a N-hydroxysuccinimide (NHS) ester, pentafluorophenyl (PFP) ester, tetrafluorophenyl (TFP) ester, aldehyde, isothiocyanate, isocyanate, sulfonyl chloride, epoxide, carbonate, aryl halide (e.g., fluorobenzene derivative), imidoester, carbodiimide, or maleimide. In certain embodiments, the photocleavable crosslinker comprises a 2-nitrobenzyl moiety and two N-hydroxysuccinimide ester moieties. In certain embodiments, the photocleavable crosslinker is bis-NHS-PC (bis-N-hydroxyl succinimide photocleavable compound) (FIG. 2, compound 5). In certain embodiments, the two electrophilic groups on the photocleavable crosslinker are the same. In certain embodiments, the two electrophilic groups on the photocleavable crosslinker are different.

In certain embodiments, the photocleavable linker moiety is cleavable by light having a wavelength of about 300 nm to about 360 nm. In certain embodiments, the photocleavable linker moiety is cleavable by light having a wavelength of about 360 nm to about 440 nm. In certain embodiments, the photocleavable linker moiety is cleavable by light having a wavelength of about 440 nm to about 500 nm. In certain embodiments, the photocleavable linker moiety in any the foregoing embodiments is not cleavable by a protease such as trypsin.

In certain embodiments, the photocleavable crosslinker comprises a fluorescent dye. Fluorescent dyes have been described herein, for example, in the section describing photochemical crosslinkers. The fluorescent dyes can be useful for imaging the cells.

Also provided are plurality of cells covalently linked to a surface using a photocleavable crosslinker as described herein and in any of the foregoing embodiments. The methods herein are useful for any type of cells.

Photolift Method: Method of Secting Cells Using Photocleavable Crosslinkers

Provided herein are methods of selecting cells with features of interest comprising the steps of: a) providing a culture of cells in a culture dish; b) attaching the cells to the surface of the culture dish and to their contacting neighboring cells using a photocleavable crosslinker as described herein; c) imaging the cells to identify a cell of interest; d) adding a protease to the culture of cells; e) illuminating the cell of interest with light, whereby the cell of interest is released from the culture dish. In certain embodiments, the method further comprises washing cells to remove unreacted photocleavable crosslinker. In certain embodiments, the step of washing cells to remove unreacted photocleavable crosslinker comprises washing the cells with a buffer. In certain embodiments, the method further comprises aspirating the released cell of interest. In certain embodiments, the method further comprises removing the cell of interest from the culture. In certain embodiments, the method further comprises continuing to grow the cell of interest. In certain embodiments, the cell of interest is subject to DNA sequencing, RNA sequencing, biochemical profiling, or proteomic analysis.

In certain embodiments, the culture dish is coated with cell adhesion proteins. In certain embodiments, the cell adhesion protein is an extracellular matrix protein. In certain embodiments, the extracellular matrix protein is fibronectin, collagen, laminin, fibrillin, vitronectin, thrombospondins, tenascins, entactins (or nidogens), nephronectin, or fibrinogen, osteopontin, agrin, aggrecan, decorin, F-Spondin, matrix extracellular phosphoglycoprotein (MEPE), nidogen-1, testican, poly-L-lysine, poly-D-lysine, poly-L-orinthine, or a combination thereof. In certain embodiments, the extracellular matrix protein is fibronectin.

In certain embodiments, the step of imaging comprises imaging the cell with a wide-field optical system comprising an objective; a means of illumination; and a camera. In certain embodiments, the means of illumination is fluorescent illumination. In certain embodiments, the means of illumination utilizes transmitted light. In certain embodiments, the step of imaging is performed with a high-speed camera. High-speed imaging can be useful for detecting, for example, neuronal action potentials. In certain embodiments, the step of imaging is performed over an extended period of time (long intervals) to detect, for example, changes in circadian period or cell growth. In certain embodiments, the step of imaging is performed using epifluorescensce microscopy, confocal microscopy, differential interference contrast microscopy, phase contrast microscopy, or Raman microscopy.

In certain embodiments, the step of illuminating the cell of interest comprises illuminating the cell with light having a wavelength of about 300 nm to about 360 nm. In certain embodiments, the step of illuminating the cell of interest comprises illuminating the cell with light having a wavelength of about 360 nm to about 440 nm. In certain embodiments, the step of illuminating the cell of interest comprises illuminating the cell with light having a wavelength of about 440 nm to about 500 nm. In certain embodiments, the step of illuminating the cell of interest comprises using patterned illumination. In certain embodiments, the patterned illumination is performed with a digital micromirror device (DMD), galvanometer mirror, acousto-optical beam deflector, or spatial light modulator (SLM).

The method provided below is an example of how the photolift method can be performed.

Cells are cultured on a surface such as a glass-bottom dish coated with cell adhesion molecules such as proteins. For example, the cell adhesion protein is an extracellular matrix protein such as fibronectin. Cell type and cell culture protocol are selected so that a subset of the cells has an attribute of interest, and this attribute is discernable using various methods such as a microscope. The cells should not pile on top of each other.

The cells are imaged, using any appropropriate cell visualization method, to identify those with the feature of interest. The protocol is agnostic to the imaging modality and the modality best suited to the feature of interest should be selected. In certain embodiments, cells are imaged in a custom wide-field optical system comprising a 2× objective with a numerical aperture of 0.5, and fluorescence illumination (for example at 488, 532, and 640 nm, depending on the fluorescent dye being used in the crosslinker). A high-speed scientific CMOS (sCMOS) camera captures images of a wide field of view (4 mm×4 mm) with high spatial (3.25 µm) and high temporal (10 ms) resolutions.

Microscope images are then processed to identify cells of interest. The protocol is agnostic to the method of cell identification. In certain embodiments, fluorescence images acquired at two or more times are compared relative to each other to identify cells that exhibited a user-defined temporal pattern of fluorescence.

Cells are nonspecifically crosslinked to each other and to the substrate in the culture dish via incubation with the photocleavable crosslinker. For example, cells are incubated with 150 µM of bis-NHS-PC (bis-N-hydroxyl succinimide photocleavable compound) in a buffer such as XC buffer (125 mM NaCl, 2 mM KCl, 15 mM HEPES, 30 mM Glucose, 1 mM $MgCl_2$, 2 mM $CaCl_2$) at 37° C. for 3-5 min following by rinsing with XC buffer to remove the unreacted bis-NHS-PC. In certain embodiments, cells are then incubated in XC buffer for another 3-5 min to ensure the crosslinking avidity between cells.

A strong protease is then added to cleave all natural protein-protein bonds linking cells to each other and to the substrate. For example, cells are incubated with a protease, such as trypsin, at 37° C. for 10-15 min. The cells still remain crosslinked to the substrate and to neighboring cells via the photocleavable crosslinker. In certain embodiments, cells are then rinsed with fresh trypsin.

Targeted cells are then illuminated with an appropriate wavelength of light, which cleaves the photocleavable crosslinks between the selected cell and its neighbors and the substrate, releasing the targeted cell. For example, for bis-NHS-PC, one or more targeted cells are illuminated with violet light (e.g., wavelength of 365-407 nm) at a dose of typically 50 $kJ/cm^2$ (corresponding to 0.5 mW over 10 µm×10 µm for 100 s).

The target cell is released from the culture. In certain embodiments, the target cell is aspirated via a glass pipette or another fluidic system for aspirating and subsequently releasing cells.

In certain embodiments, the selected cells are further processed. For example, the cells can be further grown. The cells can also be subject to DNA sequencing, RNA sequencing, proteomic analyses, or biochemical profiling.

It is understood that other variations of the above general methods are possible and are within the scope of the inventions described herein.

Applications of the Photostick and Photolift Methods

Provided herein are areas in which the photostick reagents and methods and the photolift reagents and methods can be applied both in commercial and scientific endeavors.

Modern high-resolution cameras and advanced image processing can characterize biochemically significant numbers of cells in experimentally reasonable timescales. Computational methods can select based on a vastly larger set of parameters than can be selected by biochemical or pharmacological means. The present inventions resolve the challenge of how to physically isolate cells of interest from a complex culture. Outlined below are some possible applications of the photostick and photolift technologies.

The photostick and photolift approaches could be used to identify genes whose over- or under-expression affects complex aspects of cell morphology, dynamics, or response to perturbations. Both methods could also be useful to select antibodies or other functional proteins expressed from a library at one copy per cell. Finally, photostick and photolift techniques could be used in screening unknown ion channels, orphan receptors, orphan ligands, drug-responsive proteins, and siRNA libraries.

Protein evolution. One can express at single-copy level mutants of a protein, and characterize the functional attributes of these mutants. This is useful for evolving better sensors and enzymes. Sensors: It has historically been very challenging to characterize with high throughput the response properties of genetically encoded fluorescent reporters, e.g. of voltage, $Ca^{2+}$, glutamate, or other metabolites, ions, or small molecules. With the present invention, one could express a library of candidate sensors in cells and then in parallel characterize the response of each cell to a perturbation in the concentration of the analyte. Cells showing the biggest, fastest, or most sensitive response are selected for sequencing and further evolution. This approach could also be used to evolve olfactory receptors with novel sensitivities. Enzymes: To evolve enzymes that catalyze specific reactions has also been a longstanding challenge. If the enzymatic products are (a) localized to the cell and (b) optically detectable, then the photostick protocol could be used to select enzymes with favorable kinetics or substrate affinities.

Determination of gene function. By over- or under-expressing a library of genes in single cells and then characterizing cell morphology, dynamics, or response to a perturbation, one can identify the genes that contribute to the chosen attribute.

Over-expression assays could comprise either cDNA libraries[11] or CRISPRa libraries[12]. Over-expression is useful for single-component protein machines. Multi-component complexes are difficult to identify because expressing components singly will not recapitulate the function.

Under-expression assays could comprise either Si-RNA,[13, 14] CRISPRi,[12] or CRISPR/cas9 knockout libraries.[15] Under-expression is useful when the cell already manifests the feature of interest. Under-expression is ineffective when there is functional redundancy because disabling components singly will not disable the function.

Expression libraries could be useful for de-orphanization of ligands, e.g. to find the receptor for a known ligand, or for a fluid suspected to contain an active ligand. Such assays might be used, for instance, to identify pheromone receptors by exposing libraries of G protein coupled receptors (GPCRs) to bodily fluid.

Production of transgenic cell lines. When genes are introduced to a cell by lentiviral delivery, the gene product integrates randomly into the genome. In instances where the expression level is not easily characterized by FACS (e.g. for expression of an ion channel or an olfactory receptor), the photoselection techniques can be used to select clones that show high levels of functional expression.

Identification of chaperones. For many proteins it is very difficult to attain high levels of functional expression in heterologous expression systems. This is particularly true for transmembrane proteins such as some voltage-gated ion channels (e.g. NaV 1.9) and many GPCRs (e.g. olfactory receptors). This difficulty is likely due to absence of one or more critical chaperones or trafficking factors. Expression of a target protein along with a library of other proteins could lead to better heterologous expression cell lines.

Antibody development and discovery. In the generation of monoclonal antibodies, one must select a hybridoma with high expression of functional antibodies. One could map the antibody secretion of a cell by expressing antigen on the surface, and then using a secondary fluorescent antibody to map surface-bound antibody. Cells surrounded by a bright "halo" are good candidates.

Stem cell screening. To identify genes that favor either pluripotency or a particular differentiation pathway, one could express libraries of transcription factors or other regulators and then select cells that go down the desired pathway.

Drug screening. By mutating regions of a protein and then characterizing the functional response to a drug, one could identify drug binding pockets.

Identification of functional RNAs. By expressing a library of RNAs, one could identify RNA molecules that modify cellular attributes of interest.

System for Imaging Cells

Provided herein are also systems for imaging cells comprising a plurality of cells crosslinked to extracellular matrix proteins using a photochemical crosslinker or photocleavable crosslinker as described herein, an imaging apparatus, an illuminating apparatus, and software for image processing. In certain embodiments, the system further comprises a fluidic system for aspirating and subsequently releasing single cells.

In certain embodiments, the imaging apparatus comprises a microscopic device with high magnification to perform cell selection. In certain embodiments, the imaging system comprises an objective lens (e.g., 2×, 4×, 10× objective). Various other magnification factors are possible. Various numerical aperture can be used. For example, about 0.1 to 1.0 or about 0.3 to 0.8. In certain embodiments, the microscopic device is epifluorescensce microscopy, confocal microscopy, differential interference contrast microscopy, phase contrast microscopy, or Raman microscopy. In certain embodiments, the microscopic device allows a large number of cells to be evaluated. In certain embodiments, the number of cells range between about 100 to about 10,000. In certain embodiments, the number of cells range between about 50 to 5,000. In certain embodiments, the number of cells range between about 5,000 to 15,000.

In certain embodiments, the imaging apparatus comprises a means for illuminating fluorescent dyes. In certain embodiments, the wavelength generated does not overlap with the wavelength used to activate the photochemical or photocleavable crosslinkers. In certain embodiments, the wavelength generated is greater or equal to about 480 nm. In certain embodiments, the wavelength generated is greater or equal to about 500 nm. In certain embodiments, the imaging apparatus uses dichroic mirrors to separate fluorescence light from illumination light. For example, a quad-band dichroic mirror can be useful. Sets of dichroic mirrors can be used in imaging the fluorescence onto a camera chip. Various filters such as bandpass filters can be used to filter different wavelengths of fluorescence. In certain embodiments, red fluorescence is filtered. In certain embodiments, green fluorescence is filtered. In certain embodiments, orange fluorescence is filtered.

In certain embodiments, the imaging apparatus comprises a camera. In certain embodiments, the camera is a high-speed camera. In certain embodiments, the camera captures images of a wide-field view. In certain embodiments, the wide-field view is about 4 mm×4 mm. For example, a camera can be a high-speed scientific CMOS camera that captures images of a wide-field of view with high spatial and high temporal resolution. In certain embodiments, the camera is able to image single-cells. In certain embodiments, high spatial resolution is less than 5 µm. In certain embodiments, high temporal resolution is less than about 20 ms.

The illuminating apparatus provides the appropriate wavelength of light to activate the photochemical and photocleavable crosslinkers. The light from the illuminating apparatus ideally should not overlap with the light used to generate fluorescence in the photostick method. In certain embodiments, the illuminating apparatus comprises a means for patterned illumination. In certain embodiments, the illuminating apparatus comprises a device useful for providing patterned illumination. In certain embodiments, the means or device useful for providing patterned illumination is a digital micromirror device (DMD), galvanometer mirror, acousto-optical beam deflector, or spatial light modulator. In certain embodiments, the illuminating apparatus includes a digital micromirror device that is configured to provide spatially-patterned illumination. The illumination apparatus can project spatially-patterned illumination from the digital micromirror onto the sample.

In certain embodiments, the illuminating apparatus provides a means for generating an appropriate wavelength of light for illuminating the crosslinkers and cells of interest. For example, the illumination apparatus may include a source of excitation radiation used to excite fluorescence or stimulate the sample. An exemplary illuminating apparatus is a laser. The illumination apparatus may couple one or more excitation beams into at least a portion of the imaging optical path. The illuminating apparatus can utilize mirrors to couple one or more excitation beams into a portion of the imaging optical path and acousto-optical tunable filters to modulate intensities. In certain embodiments, the laser line can be expanded to illuminate the device useful for providing patterned illumination (e.g., DMD chip), which subsequently reimages the light onto the sample plane. In certain embodiments, the illuminating apparatus projects spatially-patterned illumination from the device useful for providing patterned illumination (e.g., DMD) onto the sample (i.e., cell of interest).

The software is also part of the system for cell selection and is used to process fluorescent images from the microscopic device. In certain embodiments, manual image processing is used to identify a cell of interest. In certain embodiments, automated image processing is used to identify a cell of interest.

In certain embodiments, the system also comprises a fluidic system for aspirating targeted or un-targeted cells. In certain embodiments, a micropipette is used to aspirate cells. In certain embodiments, whole-cell aspiration is used to aspirate cells. In certain embodiments, partial-cell aspiration is used to aspirate cells. Whole-cell aspiration is used to draw an entire cell into a micropipette. Whole cell aspiration is advantageous over partial-cell aspiration in that the process does not physically contact the cell, as the fluids immediately surrounding the cell are being manipulated. Whole-cell aspiration could also be used to aspirate multiple cells simultaneously. Partial cell aspiration is used to hold the cell against a constricted micropipette tip. Partial cell aspiration alleviates the need for picoliter fluid control, and is hence easier to implement than whole-cell aspiration. Fluidic systems have been described for example in Lu, et al. "Single cell deposition and patterning with a robotic system." PloS ONE (2010) 5(10): e13542, incorporated herein by reference in its entirety.

It is understood that the foregoing detailed description and the following examples are illustrative only and are not to be taken as limitations upon the scope of the invention. Various changes and modifications to the disclosed embodiments, which will be apparent to those skilled in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

In order that the invention described herein may be more fully understood, the following examples are set forth. It should be understood that these examples are for illustrative purposes only and are not to be construed as limiting this invention in any manner.

General Methods

Photostick

Figure 1B:
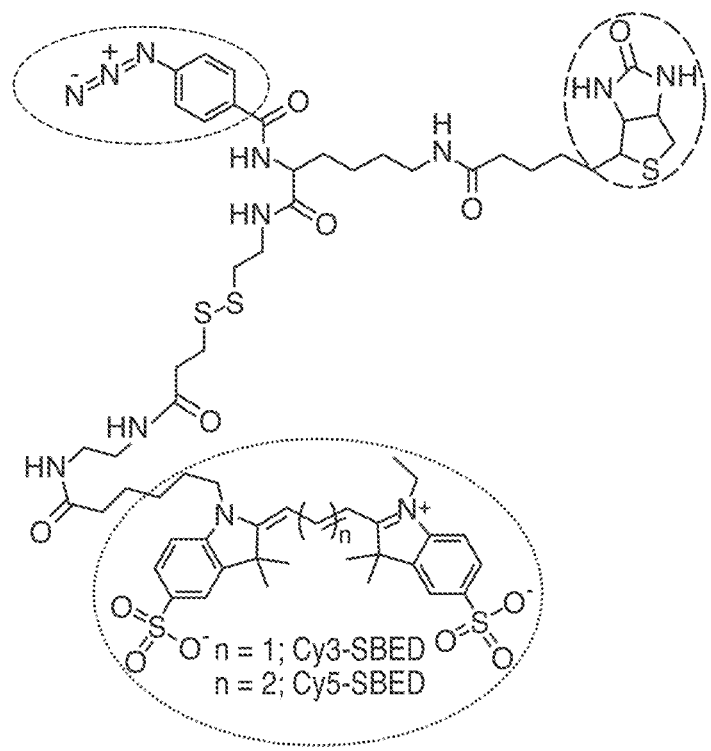

FIG. 1A illustrates the photostick protocol. Cells are cultured on glass-bottom dishes coated with fibronectin or other cell adhesion protein. Cell type and cell culture protocol are selected so that a subset of the cells has an attribute of interest, and this attribute is discernable in a microscope. The only constraint on the cell culture is that the cells must not pile on top of each other.

Cells are then imaged to identify those with the feature of interest. The protocol is agnostic to the imaging modality and the modality best suited to the feature of interest should be selected. In certain embodiments, cells are imaged in a custom wide-field optical system comprising a 2× objective with a numerical aperture of 0.5, and fluorescence illumination at 488, 532, and 640 nm. A high-speed scientific CMOS (sCMOS) camera captures images of a wide field of view (4 mm×4 mm) with high spatial (3.25 µm) and high temporal (10 ms) resolutions.

Next, microscope images are processed to identify cells of interest. The protocol is agnostic to the method of cell identification. In certain embodiments, fluorescence images acquired at two or more times are compared relative to each other to identify cells that exhibited a user-defined temporal pattern of fluorescence.

Cy3-SBED, a cell-impermeant photochemical crosslinker (FIG. 1B) is then added to the culture medium to a final concentration of 4 µM for MDCK cells, or 15 µM for neurons. This concentration may need to be adjusted between 0.4 µM and 40 µM for different cell types. Targeted cells are illuminated with violet light (407 nm wavelength) at a dose of 825 J/cm$^2$ for MDCK cells (FIG. 2), or 2200 J/cm$^2$ for neurons. The illumination is restricted to the targeted cells. In certain embodiments, the light is patterned by a digital micromirror device (DMD) positioned in an image plane of the microscope. The DMD projects patterned violet illumination targeting the cells of interest (FIG. 1C), typically with 3.25 μM spatial resolution over a 6 mm×3 mm field of view. The crosslinker immobilizes the cells on the dish.

The dish is then rinsed with buffer to remove unreacted crosslinker and un-targeted cells. In certain embodiments, the dish is incubated with ACCUTASE®, a mild protease, at 3 min, 37° C. Cells outside the illuminated region are washed away, while the illuminated cells remain adherent.

The selected cells are further processed. If further growth is desired, the cells may simply be left on the dish and maintained in culture medium in the incubator. Alternatively, the cells may be fixed and subjected to biochemical assays such as immunocytochemistry. Alternatively, the cells may be removed from the dish via a stronger protease treatment (typically trypsin) and then subject to clonal expansion, DNA sequencing, RNA sequencing, or proteomic analysis.

Photochemical Crosslinker Reagents: Cy3- and Cy5-SBED

Figure 1C:
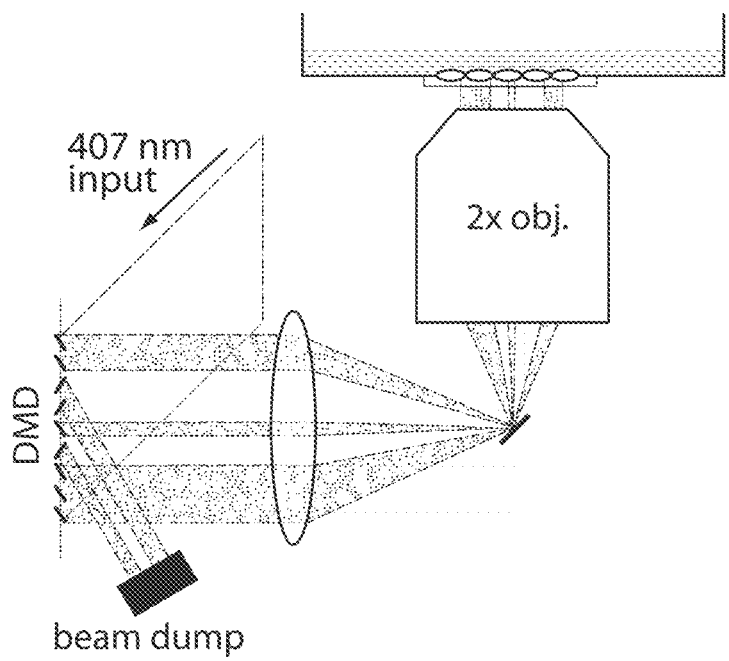

To be effective, a photostick reagent generally should not penetrate the cell membrane and should generate free radicals upon violet or near UV illumination. A nitrophenyl azide derivative was chosen for the photostick protocol. The commercially available nitrophenyl azide starting material, Sulfo-SBED ((Sulfo-N-hydroxysuccinimidyl-2-(6-[biotinamido]-2-(p-azido benzamido)-hexanoamido)ethyl-1,3'-dithioproprionate)), was conjugated with aminated fluorescent Cy3 or Cy5 dye to generate the Cy3- or Cy5-SBED product (FIGS. 1A to 1C). These molecules contained three functional groups: nitrophenyl azide, a violet light-activated radical generator; Cy3 or Cy5, a green- or red-excited, respectively, fluorescent dye; and biotin, an optional ligand used for affinity purification.

Upon violet illumination, the nitrophenyl azide dissociated and produced $N_2$ and a nitrene radical[19-21]. The nitrene radical reacted with protein functional groups via a sequential abstraction-recombination mechanism.[22,23] Radical formation on both fibronectin and cellular surface proteins led to covalent cross-linking of cells to the dish surface. Thus the illuminated cell or cells became covalently bound to the substrate; labeled with a fluorescent dye (Cy3 or Cy5); and labeled with a biotin functional group.

Synthesis of Photoactivatable Cy3-/Cy5-SBED

The two starting materials, Cy3 amine or Cy5 amine (ATT Bioquest) and Sulfo-SBED (Thermo Scientific), were combined in a one-step synthesis where the dye-free amine substituted the sulfo-N-Hydroxysuccinimide (NHS) leaving group. Sulfo-SBED (0.18 μmol, 1 equ) in DMSO (0.20 mL) was added to a solution of Cy3- or Cy5-amine (0.22 μmol, 1.2 equ) in DMSO (0.02 mL) with 2 equ of triethylamine (see Scheme 1 below). After stirring for 12 hours under nitrogen, the product was separated from unreacted dye and triethylamine via dialysis with DMSO in 1,000 MWCO dialysis tubing (Spectra). The solution was dialyzed for 1 day and DMSO solvent was replaced once during the process. After dialysis, the product identity and purity were confirmed using high resolution LC-MS where both products matched the predicted molecular weight to better than 5 ppm (Cy3-SBED: Exp. Mass: 1335.493, [M+H$^+$]: 1335.489; Cy5-SBED: Exp. Mass: 1362.509, [M+H$^+$]: 1362.503).

Scheme 1. Synthesis of Cy3- or Cy5-SBED. Sulfo-SBED (1 equ), Cy3 amine or Cy5-amine (1.2 equ), and triethylamine (2 equ) reacted in DMSO under nitrogen for 12 hrs. The product was purified by dialysis with DMSO.

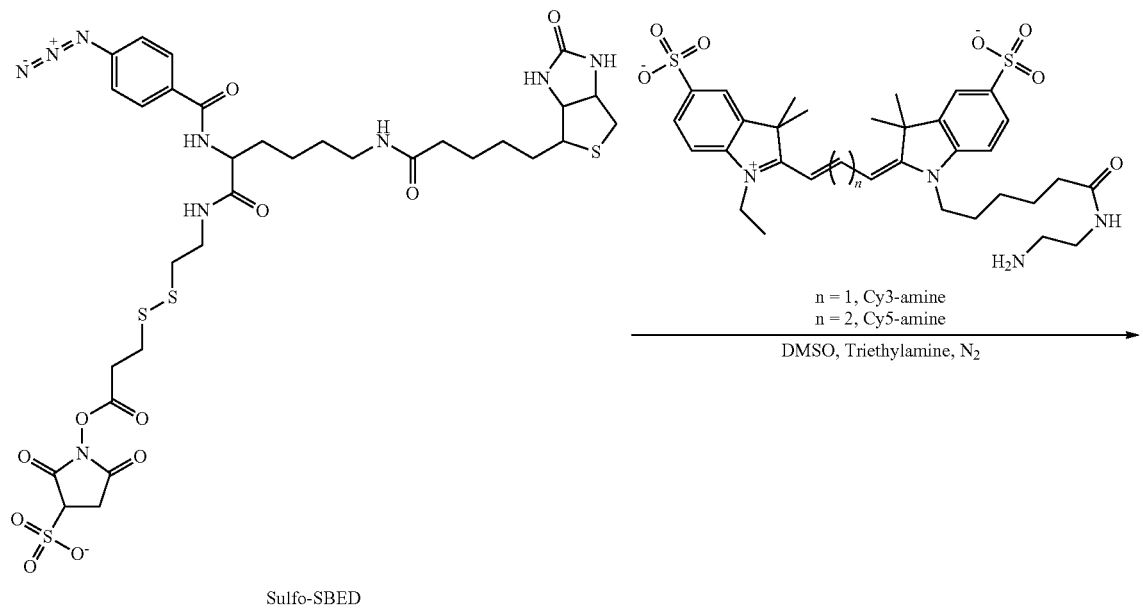

n = 1, Cy3-amine
n = 2, Cy5-amine

DMSO, Triethylamine, $N_2$

Sulfo-SBED

-continued

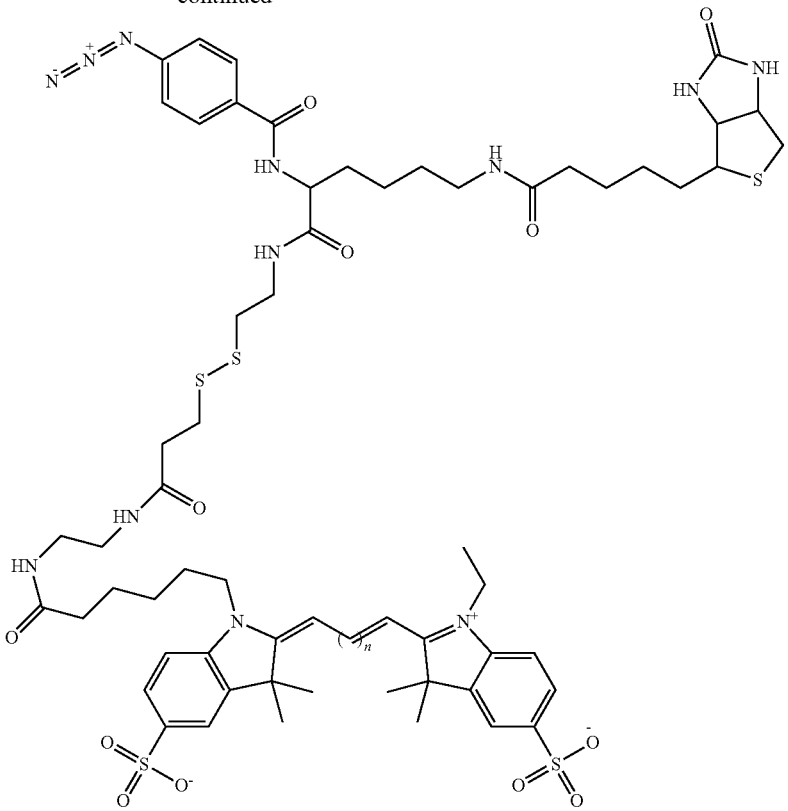

Covalent Conjugation of Fibronectin to Glass Bottom Dish

Glass-bottom dishes (In Vitro Scientific, D35-14-1.5-N) were cleaned and chemically activated by 5 min treatment in a plasma cleaner with low-pressure ambient air. The glass was aldehyde-functionalized with a 1% solution of 11-(Triethoxysilyl) undecanal (Gelest, Inc.) in ethanol, which reacted for 1 hour in a nitrogen-purged container. Dishes were rinsed twice with ethanol and once with nanopure water and then cured in a vacuum oven at 65° C. for 1-2 hours to drive off remaining water or alcohol and complete the glass-silane bond.

Fibronectin (0.1 mg/mL in PBS) was added to the dishes and incubated overnight at 4° C. or at 37° C. for 2 hours, resulting in a covalent imine bond between the surface and free primary amines on the fibronectin.[31] After incubation with fibronectin, dishes were immersed in 0.1% Tween-20 PBS for 10 min followed by rinsing three times with PBS. Completed dishes could either be seeded with cells directly or stored at −80° C.

MDCK (Madin-Darby Canine Kidney) Cell Culture

MDCK epithelial cells were grown in DMEM supplemented with 10% FBS and penicillin/streptomycin in a 37° C. incubator under 5% $CO_2$. Cells were grown to 50-70% confluency in 3.5 cm dishes and transfected with a mammalian expression vector coding for YFP under the CMV promoter (pDisplay-AP-YFP) using TransIT-X2 (Mirus). 24-48 hours after tranfection, cells were trypsinized and re-plated at a density of ~32,000-35,000 cells/$cm^2$ on fibronectin-coated glass bottom dishes (described above). Experiments were performed 12-24 hours after plating on the glass-bottom dishes.

Neuronal Cell Culture

Sprague Dawley rats were obtained from Taconic Labs. Postnatal day 0 (P0) pups were euthanized and hippocampi were dissected following the procedure in Ref. (32). Briefly, isolated hippocampi were digested with papain and homogenized in Hank's Balanced Salt Solution (HBSS) containing $MgCl_2$ and kyneurinic acid to prevent excitotoxicity. After dissociation, neurons were electroporated (Lonza, Nucleofector electroporation kit) with pLenti-hsyn-Optopatch (1 µg for 1 million neurons) and plated on glass-bottom dishes coated with covalently-bound fibronectin (described above) at a density of ~45,000/$cm^2$. Neurons were initially cultured in plating medium [MEM (Life Technologies) containing 10% fetal bovine serum, 0.5% glucose, 10 mM HEPES, 2 mM Glutamax (Life Technologies), 100 mg/L transferrin, insulin, and B27]. After 3 days, the medium was replaced with NbActiv4 (Brainbits, Nb4-500). At 4 days in vitro (div) 2 µM AraC was added to suppress further glial growth. At 7-14 div, electroporated neurons were ready for experimentation.

All experimental protocols involving use of animals were approved by the Harvard Institutional Animal Care and Use Committee (IACUC).

Optopatch Measurements

Optopatch experiments were conducted on a home-built inverted fluorescence microscope described in Ref. (26). Briefly, illumination was provided by six lasers at 635 nm, 500 mW (Dragon Lasers 635M500), combined in three groups of two. Illumination was coupled into the sample using a custom fused silica prism, without passing through the objective. Fluorescence was collected by the low-magnification objective (Olympus 2×MVX Plan Apochromat), passed through an emission filter, and imaged onto a scientific CMOS camera (Hamamatsu Orca Flash 4.0). This microscope imaged a 1.2×3.3 mm field of view with 3.25 µm spatial resolution and 2 ms temporal resolution.

Blue light illumination for channelrhodopsin stimulation was provided by a 473 nm, 1 W laser (Dragon Lasers), modulated in intensity by an acousto-optic modulator and modulated spatially by a digital micromirror device (DMD, Digital Light Innovations DLi4130-ALP HS). The DMD was re-imaged onto the sample via the 2× objective. The DMD provided targeted stimulation with 3.5 µm spatial resolution and 0.1 ms temporal resolution. For the Optopatch measurements, neurons were stimulated with seven, 500 ms duration pulses of blue light. Stimuli lasted 500 ms, and the intensity of successive pulses increased from 0 to 58 mW/cm$^2$.

Between stimuli, cells were given 5 s recovery in the dark. Fluorescence traces were extracted from the raw movies as described in Ref. 26.

Neuronal Electroporation

Neuronal electroporation reagents were purchased from Lonza and the Nucleofector electroporation kit (Lonza) was used following the standard protocol. Briefly, 1.5 µg of pLenti-hsyn-Optopatch plasmid and 1.5 million rat hippocampal neurons were added to 100 µL of Nucleofector solution. The mixture was transferred to an electroporation cuvette and cells were shocked using Nucleofector program G-013. After electroporation, 500 µL of plating culture medium was added to the cuvette and the sample was gently transferred into the prepared fibronectin-conjugated glass-bottomed dishes at a concentration of 45,000 cells/cm$^2$. After 2 h of incubation (37° C., 5% $CO_2$), plates were rinsed to remove unbound neurons and then filled with 1 mL of fresh plating medium. Typical transfection efficiencies were ~50%.

Photostick Optics

Photostick experiments at high magnification were performed on a custom-built microscope. Illumination light was provided by either a 637 nm 140 mW Coherent Obis, a 488 nm 100 mW Coherent Obis, or a 405 nm 30 mW Dragon Laser. Laser lines were combined with dichroic mirrors and intensities were modulated using acousto-optical tunable filters (Gooch & Housego). The 488 nm laser line was expanded to illuminate the chip of a DMD (Texas Instruments DLP LightCrafter with DLP 0.3 WVGA chipset) which was subsequently reimaged onto the sample plane. The 637 nm and 488 nm lines were focused at the back focal plane of a LCPlanFl 20× 0.40 NA objective (Olympus). Collimated 405 nm laser light at the back focal plane of the objective was defocused to obtain a 5 µm spot at the sample and was steered in the sample plane using galvo mirrors (Thorlabs GVS202) located in a conjugate plane. Fluorescence light was separated from illumination light using a quad-band dichroic mirror (Semrock #Di01-R405/488/561/635). The fluorescence was then imaged using a custom dual-wavelength imaging system. A rectangular aperture in an image plane set the boundaries of the image. The fluorescence was then split into two channels using a dichroic mirror (Semrock FF662-FDi01) and then recombined on a second dichroic mirror (Semrock FF662-FDi01) and reimaged onto adjacent halves of the chip of a scientific CMOS camera (Hamamatsu Orca Flash 4.0). Red fluorescence was filtered using a HQ700/75m bandpass filter (Chroma). Green and orange fluorescence was filtered using a HQ550/50m bandpass filter (Chroma).

Photostick experiments at low magnification were conducted on a home-built inverted fluorescence microscope described in the Optopatch measurement section above. A 407 nm 200 mW Laser (Lilly Electronics) was modulated spatially by a DMD which was re-imaged onto the sample via the 2× objective. The DMD provided targeted violet stimulation with excitation with 3.25 µm spatial resolution.

Example 1

Photostick Method with 4-fluoro-3-nitrophenyl azide (FNPA)

Initially, the photostick protocol was tested with a water soluble phenyl azide radical initiator, 4-Fluoro-3-nitrophenyl azide (FNPA, FIGS. 8A to 8D). Upon exposure to violet light (407 nm), this compound releases $N_2$ and produces a nitrene radical[19-21] that reacts with protein functional groups via a sequential abstraction-recombination mechanism.[22, 23] Radical formation on both fibronectin and cellular surface proteins leads to covalent crosslinking of cells to the dish surface. FNPA was added at a concentration of 4 µM to cultures of epithelial MDCK cells and exposed to patterned 407 nm light (825 J/cm$^2$). The pattern was developed via incubation with ACCUTASE® (3 min, 37° C.) followed by rinsing with buffer. The remaining cells clearly followed the 50 illumination pattern (FIGS. 8A to 8D).

FNPA has a calculated octanol/water partition coefficient of Log P=3.0, implying high membrane permeability.[24] Therefore, there was a possibility that this initiator could enter the cells, crosslinking internal components and perturbing cell physiology. Furthermore, other than the cells' location on the dish, there was no clear indication of which cells had been targeted for selection. In certain cases, a cell-permeable crosslinker is not desired. Therefore, two trifunctional photochemical crosslinkers, Cy3- and Cy5-SBED, were synthesized by reacting an aminated fluorescent dye (Cy3 or Cy5) with sulfo-SBED (Sulfo-N-hydroxysuccinimidyl-2-(6-[biotinamido]-2-(p-azido benzamido)-hexanoamido)ethyl-1,3'-dithioproprionate) (FIG. 1B). The product contained a fluorescent group, a biotin group, and an aryl azide photochemical radical initiator. The two sulfate groups and the large size of the construct suggested that it would show poor membrane permeability, while the dye allowed easy tracking. The biotin gave the option for downstream labeling with streptavidin, but was not used in this study.

Figure 4A:
FIGS. 4A-4F show photostick of MDCK cells with sequential addition of Cy3-SBED and Cy5-SBED.
Figure 4B:
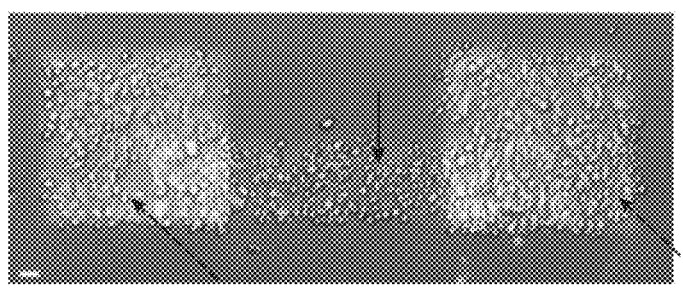
Figure 4C:
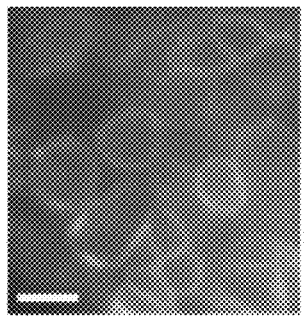
Figure 4D:
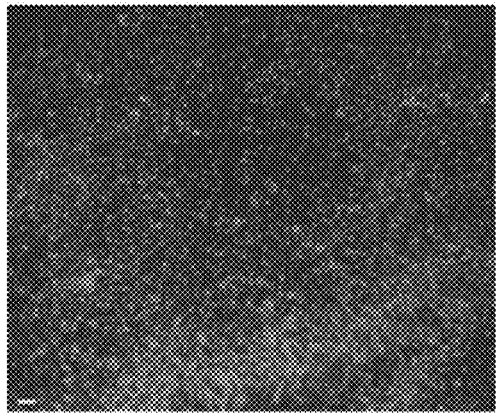
Figure 4E:
Figure 4F:
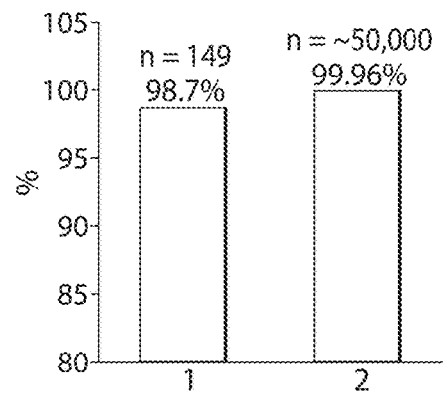
Figure 5E:
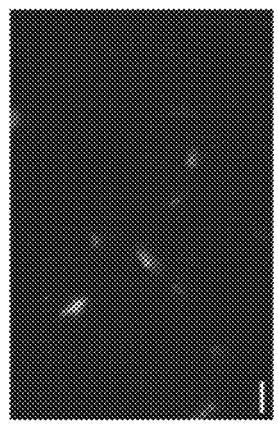
FIGS. 5A-5H show a photostick of target cells.
Figure 5G:
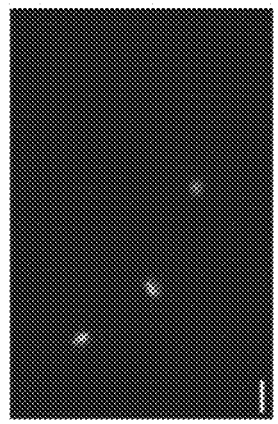
Figure 5D:
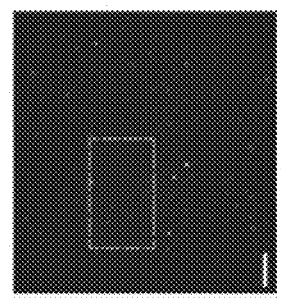
Figure 5F:
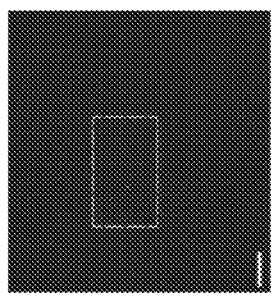
Figure 5C:
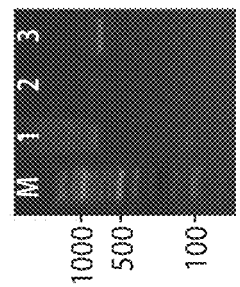

The selectivity of the photostick protocol was quantified as a function of Cy3-SBED concentration and illumination dose (FIGS. 9A to 9E and 10A to 10E). The optimal conditions depended on cell type, e.g. 4 µM Cy3/5-SBED at light dose 825 J/cm$^2$ was optimal for MDCK cells (FIGS. 4A to 4F and 9A to 9E), while 15 µM Cy3/5-SBED at light dose 2200 J/cm$^2$ was optimal for neurons (FIGS. 5C and 5D). To test the viability of cells after a photostick procedure, a dish of patterned MDCK cells was returned to the incubator. A live-dead stain showed 98% live cells subsequent to a photostick protocol (FIGS. 11A to 11D). The cells continued to migrate and divide (FIGS. 12A to 12F) with a doubling time of 34 h.

Example 2

Photostick on MDCK Cells Via Cy3- and Cy5-SBED

Methods

MDCK cells were seeded at a density of 32,000/cm$^2$ on fibronectin-coated glass-bottomed dishes. Immediately prior to the photostick protocol, Cy3-SBED was added to the imaging medium to a final concentration of 4 µM. The cells were illuminated with two squares of 407 nm light (825 J/cm$^2$). After 15 min illumination, the dish was rinsed 3 times with DPBS (PBS without calcium and magnesium) before adding the second photoactivatable crosslinker, Cy5-SBED (4 µM). A rectangular bar was illuminated using the same procedure for another 15 min. The dish was then treated with ACCUTASE® for 3 min to detach the cells that had not been illuminated. The patterned MDCK cells were imaged using white light trans-illumination and the bound dyes were visualized via fluorescence (Cy3: $\lambda_{ex}$=530 nm, $\lambda_{em}$=574/40 nm BP; Cy5: $\lambda_{ex}$=637 nm, $\lambda_{em}$=665 nm LP).

Experiment

Figure 13A:
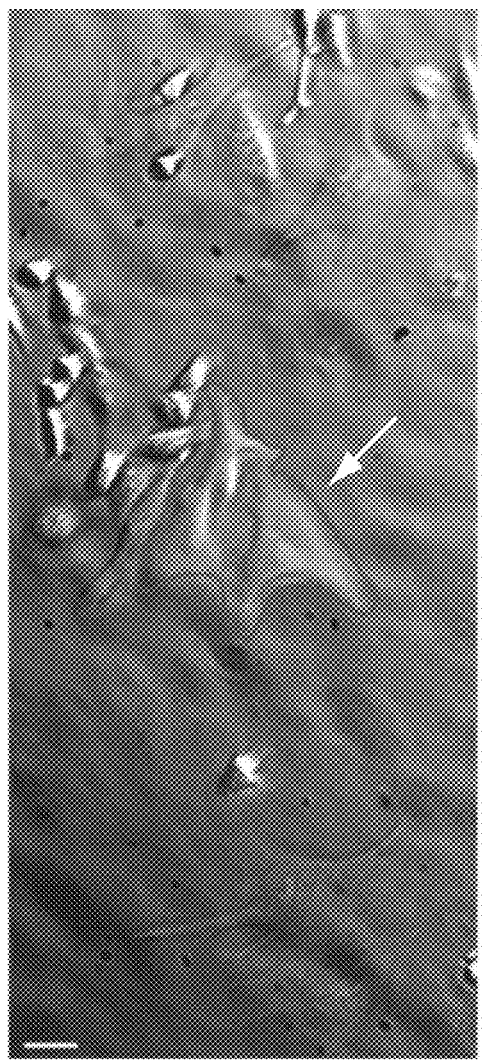
FIGS. 13A-13B show the process of using photostick to select multiple YFP-MDCK cells. 4 µM of photoactivatable Cy3-SBED was added in the dish and 407 nm light (8200
Figure 13B:
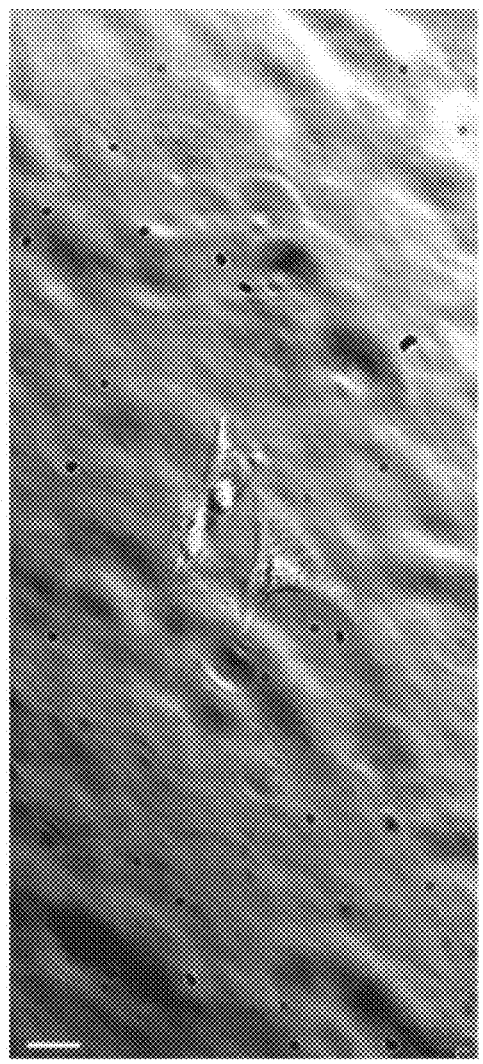

Successive photostick protocols were performed on a sample of MDCK cells (FIGS. 4A-4B), first with a green dye, Cy3-SBED (4 µM, 825 J/cm$^2$), and then with a red dye, Cy5-SBED. Upon wash-out of the dyes, the illuminated cells showed strong 15 fluorescence corresponding to the color dye with which they were exposed. No difference in Cy5 labeling efficiency was detected between the cells that had already been labeled with Cy3 and the cells that had not, indicating that a small fraction of reactive sites on the cell surface were occupied by each dye. Incubation with ACCUTASE® (3 min, 37° C.) detached the un-exposed cells while leaving the exposed cells (FIG. 4B). High magnification images (FIG. 4C) showed that the fluorescence was localized to the cell membrane. Absence of intracellular fluorescence confirmed that the dye-SBED compounds did not enter the cells. In nine repeated trials, 98.7% (147 of 149) photostuck cells remained (FIG. 4F, bar 1), while 0.04% (21 of ~50,000) of non-photostuck cells remained (FIG. 4F, bar 2; see also FIGS. 13A to 13B). Thus, the photostick method has high selectivity, specificity and accuracy for the targeted cells (FIG. 4F). FIGS. 4D-4E show a low-magnification field of view of MDCK cells before (FIG. 4D) and after (FIG. 4E) the photostick protocol.

Example 3

Selection of Single Clones from Genetically Heterogeneous Culture

Protocol

Photostick on YFP-Transfected MDCK Cells Via Cy5-SBED from a Pool of YFP- or Non-YFP-Expressing Cells YFP-transfected MDCK cells were seeded at a density of 32,000/cm$^2$ on fibronectin-coated glass-bottomed dishes. This photostick experiment was conducted on a custom-built microscope at high magnification as described above. A YFP fluorescence image was recorded ($\lambda_{ex}$: 488 nm, $\lambda_{em}$: 525/36 nm BP) to identify potential photostick targets. The photochemical crosslinker Cy5-SBED was added to a final concentration of 4 µM. Light at 407 nm was directed exclusively onto a YFP-MDCK cell with a galvometric mirror pair. Subsequently, the dish was rinsed with DPBS and digested with ACCUTASE® to detach non-illuminated cells. The remaining adhered cells were lysed with DNA Extract kit (Life Technologies; see below for details) and the lysate was analyzed via PCR (FIG. 5G) and gene sequencing. The primers for PCR of YFP were: YFP-primer-fwd: gcaagggc-gaggagctgttca (SEQ ID NO: 1); YFP-primer-rev: ccgcttg-tatagctcgtccatgcc (SEQ ID NO: 2).

Photostick on YFP-Transfected MDCK Cells Via Cy5-SBED from a Pool of YFP- or mOrange-Expressing Cells YFP-transfected MDCK cells were seeded at a density of 32,000/cm$^2$ on fibronectin-coated glass-bottomed dishes. This photostick experiment was performed on a home-built inverted fluorescence microscope at low magnification as described above. A YFP fluorescence image was recorded ($\lambda_{ex}$: 488 nm, $\lambda_{em}$: 525/36 nm BP) to identify potential photostick targets. For mOrange fluorescence imaging, excitation at 535 nm and emission at 575/40 nm BP were used. The photochemical crosslinker Cy5-SBED was added to a final concentration of 4 µM. Light at 407 nm was directed exclusively onto three YFP-MDCK cells with a DMD. Subsequently, the dish was rinsed with DPBS and digested with ACCUTASE® to detach non-illuminated cells. The remaining adhered cells were lysed with DNA Extract kit (Life Technologies; see below for details) and the lysate was analyzed via PCR (FIG. 5H) and gene sequencing. The consensus primers for PCR (used in lane 1, 3, and 4, FIG. 5H) of YFP and mOrange genes were: Con-fwd: ggaattcg-gcttggggatatccacc (SEQ ID NO: 3); Con-rev: ggcaccacgat-gacctcctgc (SEQ ID NO: 4). For mOrange specific primers in Lane 2 (FIG. 5H) were: mO2-fwd: gtgagcaagggcgagga-gaataacat (SEQ ID NO: 5); mO2-rev: ccgcttgtacagctcgtc-catgc (SEQ ID NO: 6).

Single- or Few-Cell PCR

After the photostick protocol and ACCUTASE® development, the dish was rinsed thoroughly with PBS to remove residual non-target cells. Complete removal of non-target cells was verified by examination in the microscope. The target cells were then detached from the dish by incubation with trypsin for ~3 min. The trypsin was then diluted by addition of an equal volume of PBS. The supernatant containing the selected cells was centrifuged at 10,000 rpm for 2 min. After discarding the supernatant, the cells were lysed with the DNA Extract All kit (Life Technologies 4403319), as follows: cells were resuspended with 2 µL of PBS buffer and gently pipetted up and down a few times, and then 20 µL of Lysis Solution was added to the cells and reacted at room temperature for 3 min. Next, 20 µL of DNA Stabilizing Solution was added. Samples were either amplified by PCR immediately, or stored at −20° C. before amplification. Finally, standard PCR procedures were carried out from the cell lysate.

Experiment

A natural application of the photostick technique is to select single clones from a genetically heterogeneous culture. These clones could be produced e.g. by library lentiviral knockdown of endogenous genes,[25] or by overexpression of a library of functional endogenous or heterologous genes. Thus, the suitability of the photostick protocol for genetic profiling of single cells selected from a heterogeneous culture was tested.

First, whether genetic information could be retrieved from a single cell selected by photostick was tested. MDCK cells expressing YFP were plated sparsely in a background of non-expressing cells (FIG. 5A). A single YFP-positive cell was selected by photostick (4 µM Cy5-SBED). After ACCUTASE® treatment (3 min, 37° C.), only the single targeted cell was visible (FIG. 5B). The selected cell was then released via trypsinization, and its genetic content was analyzed by single-cell PCR (described above). The YFP gene product was detected (FIG. 5C, lane 1). The experiment was repeated with selection of a cell lacking YFP expression. No YFP gene product was detected (FIG. 5C, lane 2).

Next, whether genetic information from surrounding cells could contaminate the genetic material amplified from the cell selected by photostick was tested. Such contamination could arise, for instance, by lysis of surrounding cells; or by surrounding cells remaining adhered during the ACCUTASE® treatment but then being released by trypsin.

Figure 5H:
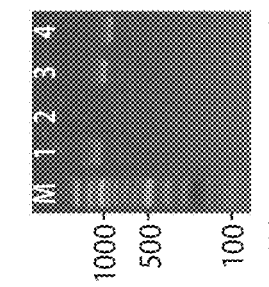
Figure 5B:
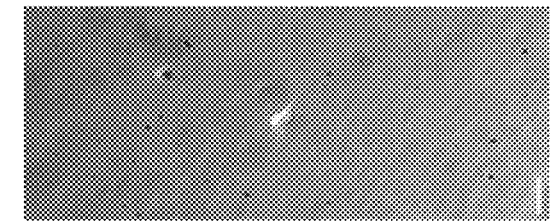
Figure 5A:
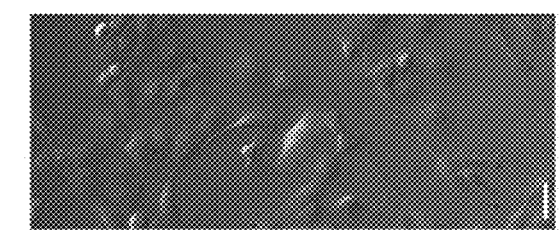

In FIGS. 5A to 5H, three YFP-positive cells were selected by photostick (4 µM Cy5-SBED) out of a background population dominated by cells expressing mOrange. After ACCUTASE® treatment only these three cells remained (FIGS. 5D-5G). These cells were released with trypsin. Amplification with consensus primers for YFP and mOrange led to a single band (FIG. 5H, lane 1). Amplification with primers selective for YFP only also led to a single band (FIG. 5H, lane 2). Amplification with primers selective for mOrange did not produce a product (FIG. 5H, lane 3). These results established that mOrange DNA from the surrounding cells did not contaminate the photostick-selected YFP-expressing cells, despite the large number of mOrange-expressing cells initially in the population.

Example 4

Cell Selection on Basis of Complex Functional Parameter

Protocol

Rat hippocampal neurons were electroporated with the Optopatch vector and then seeded on fibronectin-coated glass-bottomed dishes and cultured for 7-14 days. 30 min before Optopatch measurements, 5 µM all-trans retinal was added to culture medium to enhance QuasAr2 fluorescence and voltage sensitivity. Immediately prior to Optopatch measurements, the cellular medium was exchanged to the low auto-fluorescence XC buffer (125 mM NaCl, 2.5 mM KCl, 2 mM $CaCl_2$, 1 mM $MgCl_2$, 10 mM HEPES, 30 mM glucose, pH 7.3). Neuronal action potentials were induced using the stepped stimulus protocol described above. A neuron displaying an unusual rapidly inactivating firing pattern was chosen for subsequent photostick selection. The photo-crosslinker Cy3-SBED was added to a final concentration of 15 µM and 407 nm light was directed selectively onto the specified neuron (2200 $J/cm^2$). After exposure, the dish was rinsed with XC buffer and non-illuminated cells were detached with ACCUTASE®. The remaining adhered cells were lysed and the lysate was analyzed via PCR (FIG. 6D) and gene sequencing. The primers for PCR of Optopatch were: Optopatch primer-fwd: atcgctctgcaggctggttacgac (SEQ ID NO: 7); Optopatch primer-rev: tcggcaccggcactggg (SEQ ID NO: 8).

Experiment

Figure 6A:
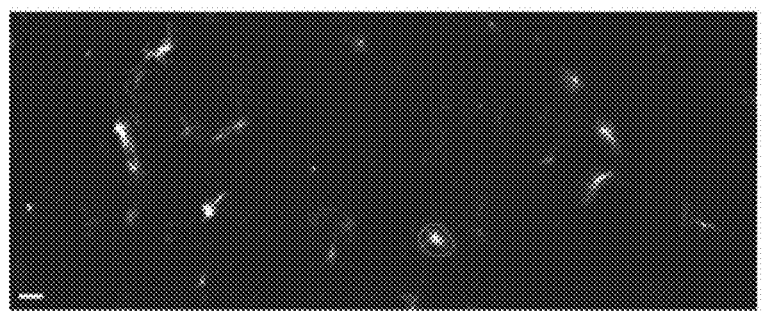
FIGS. 6A-6D show the photostick of a single neuron with rapidly adapting firing pattern (FIG. 6C, arrows) as determined by Optopatch measurement.
Figure 6B:
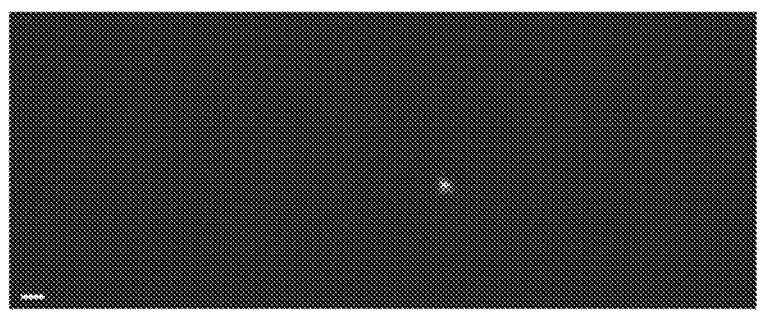
Figure 6C:
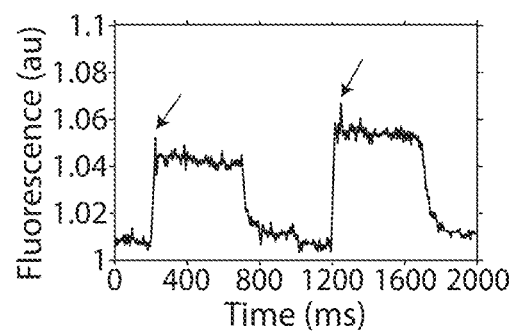
Figure 6D:
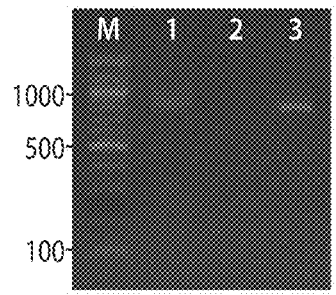
Figures 7A, 7B, 7C, 7D:
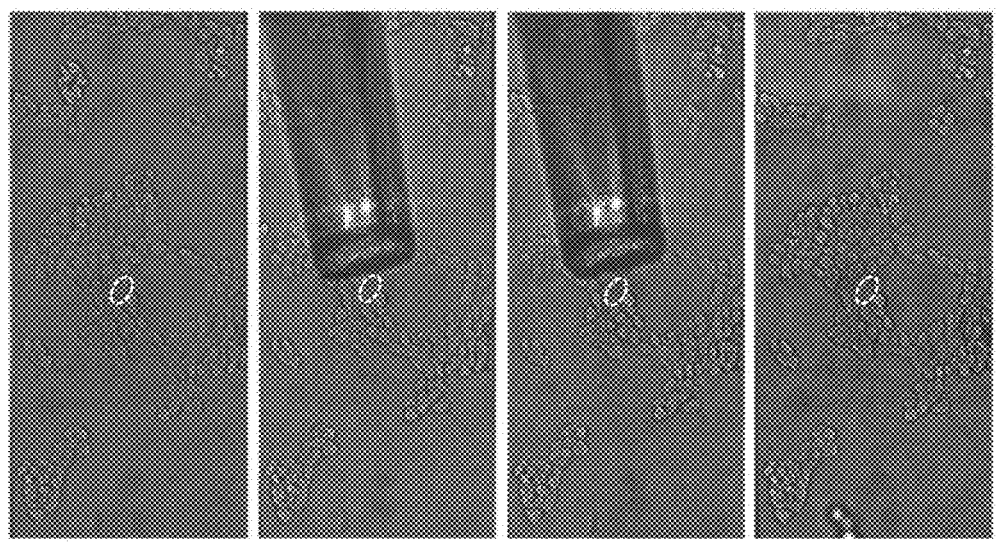
FIGS. 7A-7D demonstrate the selection of single HEK cell from culture via the photolift technique. Here the cells are visualized via transmitted light, although any fluorescence imaging modality could be used instead.
Figure 8D:
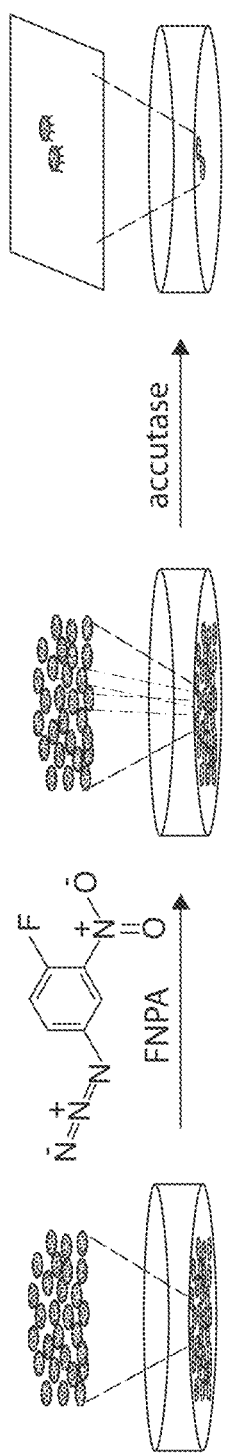
Figure 8D:
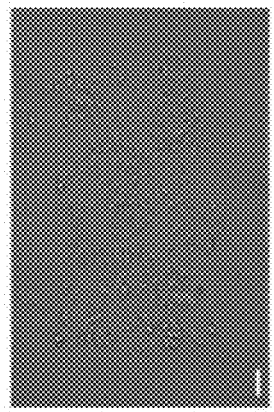
Figure 8C:
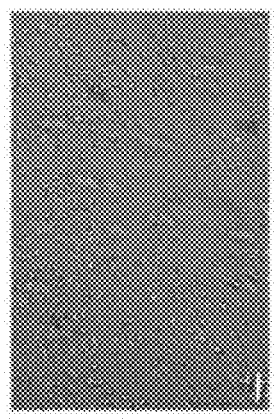
Figure 8B:
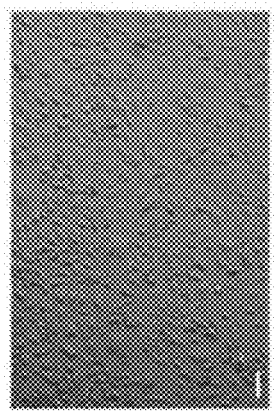
Figure 9E:
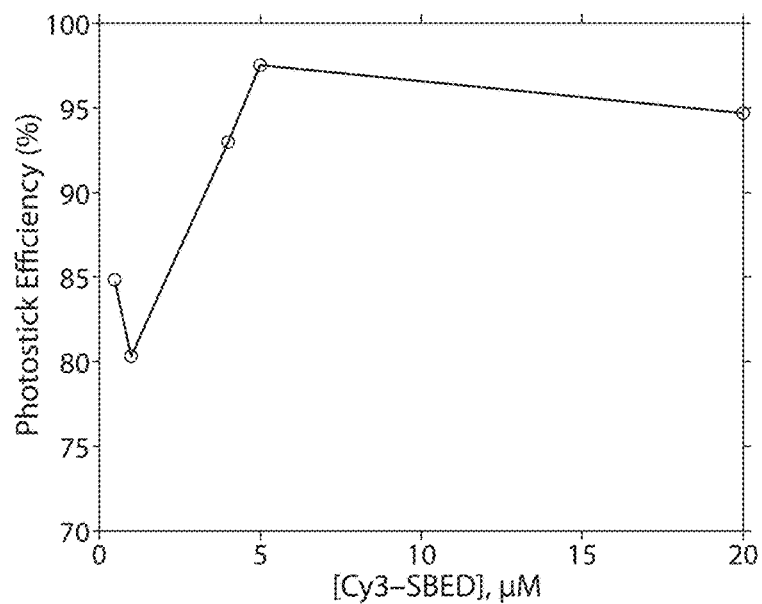
FIGS. 9A-9E show photosticking efficiency as a function of Cy3-SBED concentration (graph.
Figure 9A:
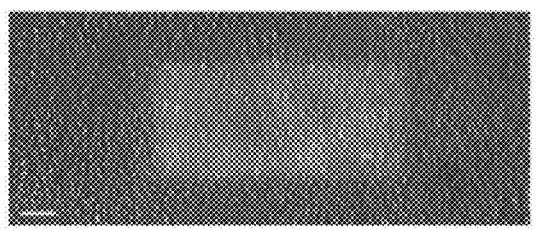
Figure 9B:
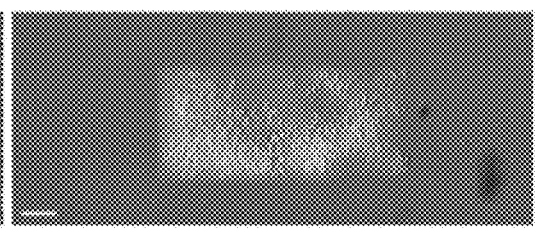
Figure 9C:
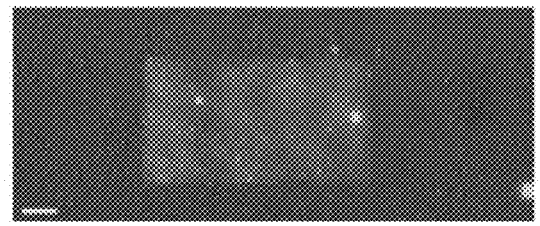
Figure 9D:
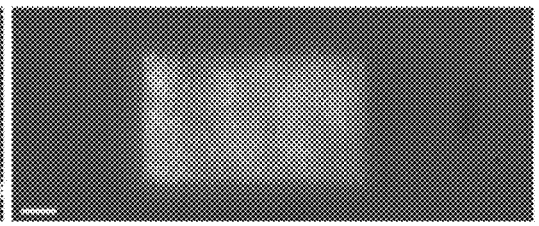
Figure 10E:
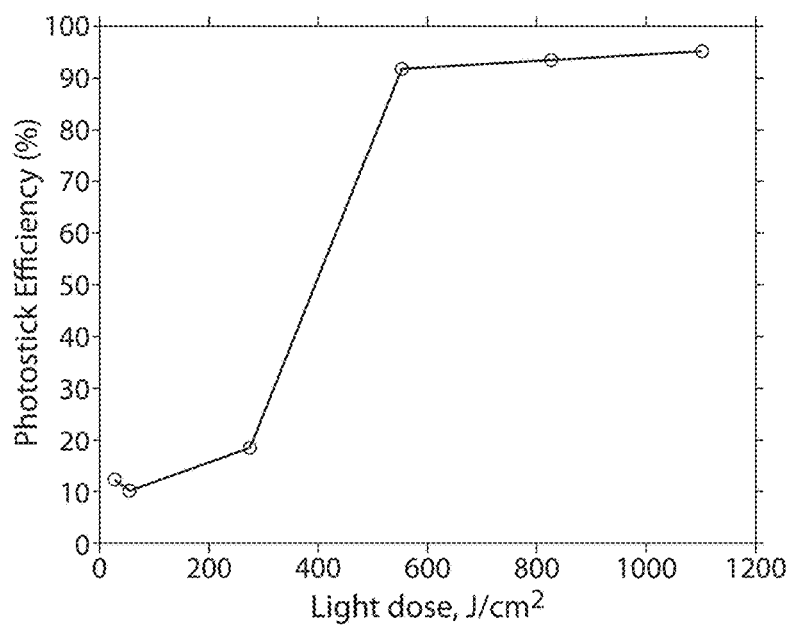
FIGS. 10A-10E show photosticking efficiency as a function of 407 nm light dose (graph.
Figures 10A, 10B:
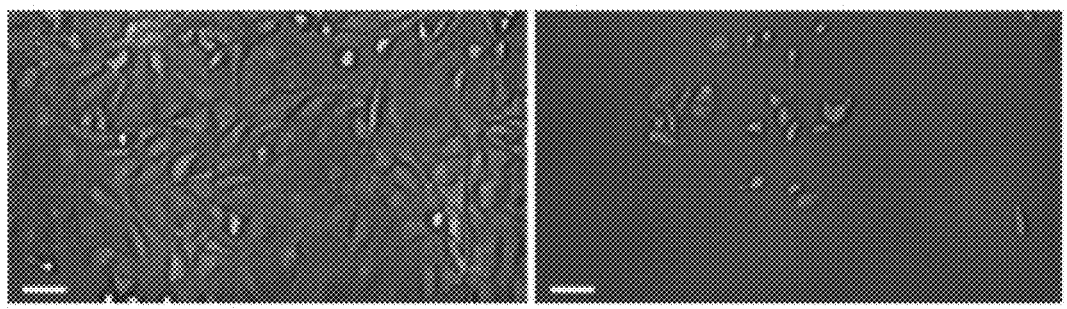
Figures 10C, 10D:
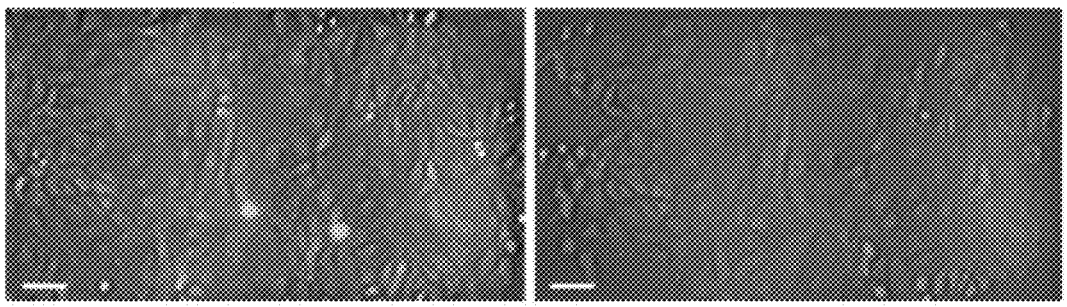
Figures 11A, 11C:
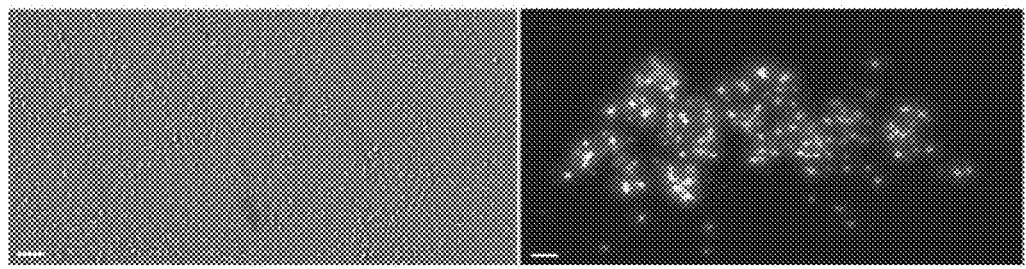
FIGS. 11A-11D show the effect of photostick protocol on cell viability. MDCK cells were subjected to the photostick protocol (illumination dose 825 J/cm$^2$, 4 µM Cy5-SBED).
Figures 11B, 11D:
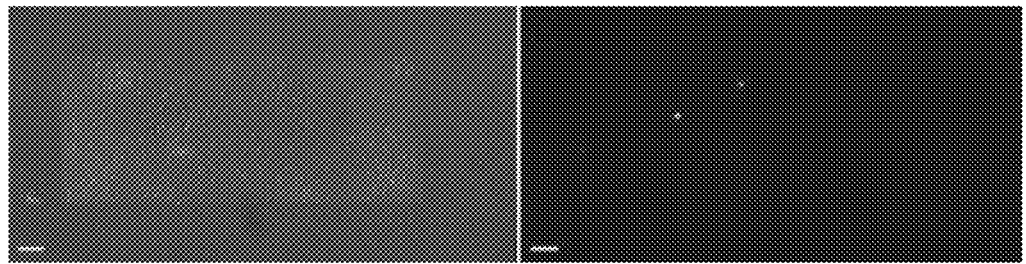
Figure 12A:
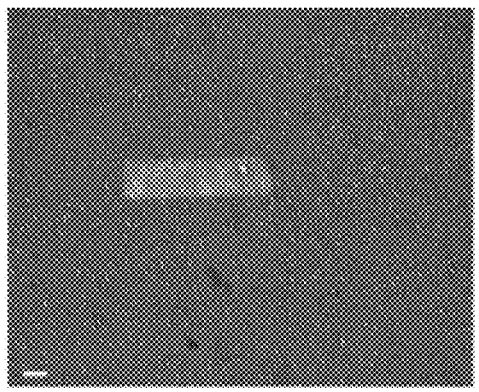
FIGS. 12A-12F show the effect of the photostick protocol on MDCK cell growth rate. MDCK cells were treated with 4 µM Cy3-SBED and then exposed to a rectangle of 407 nm light (825 J/cm$^2$).
Figure 12B:
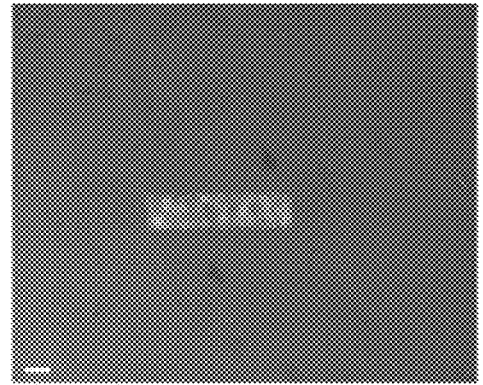
Figure 12C:
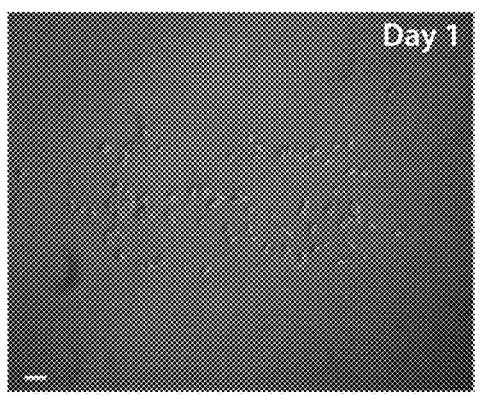
Figure 12D:
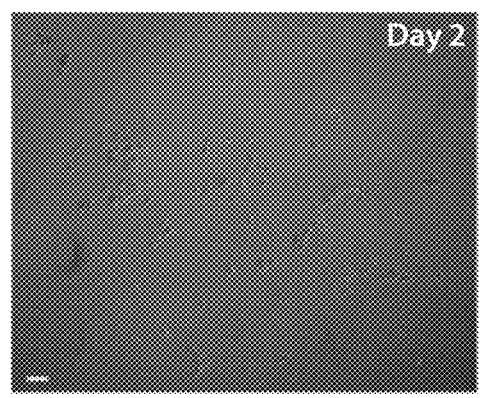
Figure 12E:
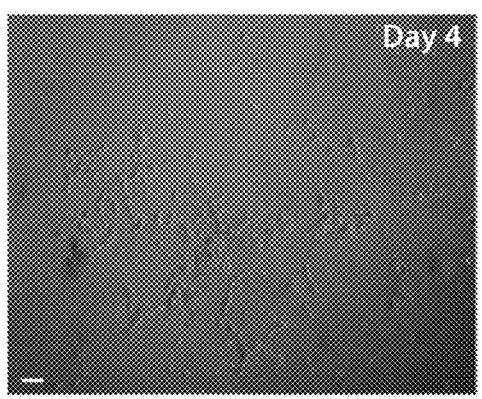
Figure 12F:
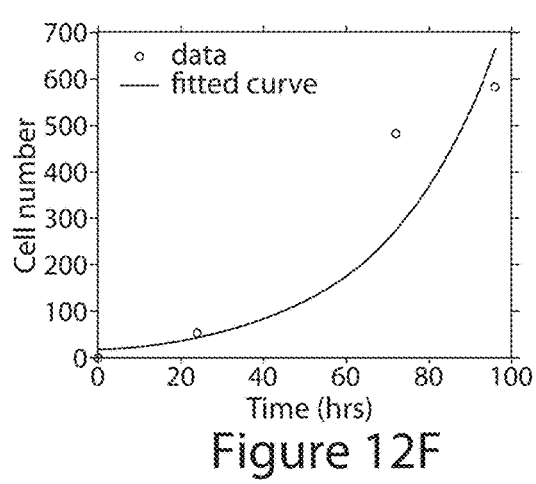

The ability to select cells on the basis of a complex functional parameter was tested. A platform for all-optical electrophysiology ("Optopatch") in cultured neurons has been recently developed.[26] The Optopatch construct was expressed in cultured rat hippocampal neurons, and used a wide-field imaging system for simultaneous optical stimulation and optical recording from a field of view containing ~40 neurons expressing the Optopatch construct. A neuron that showed a rapidly adapting firing pattern was chosen (FIG. 6C), Cy3-SBED (15 µM) was added to the imaging medium, and the cell was selected via photostick (FIG. 6A). After incubation with ACCUTASE® (6 min. 37° C.), the selected neuron remained, while the other neurons had been washed away (FIG. 6B). The photostick protocol kept the cell body, but not the distal neurites. PCR recovered the Optopatch genes from the selected cell (FIG. 6D) and subsequent sequencing recovered the complete gene sequence.

Conclusions

The 407 nm light used for photostick is not directly absorbed by proteins or nucleic acids, but could excite cofactors such as FAD. The photostick protocol preserved the viability of MDCK cells, but one may worry about more subtle cellular perturbations or stress associated either with the violet light exposure or with the covalently bound dyes. The significance of these perturbations depends on the application. When the selected cells are immediately fixed or lysed for biochemical analysis (e.g. DNA or RNA sequencing, or proteomics) optical perturbation effects will likely be minor, due to the short interval between violet illumination and cell harvest. When the selected cells are to be grown into a stable cell line, optical perturbation effects will also likely be minor, due to the many generations of growth required before use, providing time for cells to recover. However, when the selected cells will be used for functional assays shortly after selection, it is advisable to use appropriate control experiments to test for illumination artifacts.

Each cell type and culture protocol will likely require optimization of the parameters. A two-step procedure is recommended: first, without using the photostick protocol, one should determine the minimum ACCUTASE® incubation time to lift the cells. This determination can be performed in a single dish by gently pipetting the ACCUTASE® solution and periodically checking for cell detachment. Second, one should determine the concentration of Cy3- or Cy5-SBED and illumination dose to achieve ACCUTASE®-resistant adhesion, starting from the parameters presented here. Cells adhered by the photostick protocol will not be detached by the shear associated with gentle rinsing. The photostick protocol worked with substrates coated with either fibronectin or poly-D-lysine, and similar results are anticipated with any surface presenting primary amines (e.g. lysine) or hydroxyl groups (e.g. serine).

For screening applications, one is particularly concerned about the proportion of false positives among the selected cells. Suppose there are N cells initially on the dish, the false-positive rate is f (cells that should be washed away but remain), and the true positive rate is p (cells that should remain and do remain). To achieve a ratio, R, of true-positive to false-positive cells, one should select n=R N f/p cells. In the experiments, the false positive rate ranged from 0 to 2%, with the undesired cells often adhering around a defect in the dish. Through careful attention to preparation of the dish, one can minimize f. By increasing the ACCUTASE® incubation time one can further decrease f at the expense of a modest decrease in p. One can increase the illumination dose or the concentration of crosslinker to maximize p. Under strong illumination, scattered light can crosslink cells adjacent the desired cell. It was found that selections worked best with MDCK cells, whose large size facilitated single-cell selection. In highly confluent cultures of HEK cells, application of photostick to a single cell often retained one or more of its adjacent neighbors as well.

Modern high-resolution cameras and advanced image processing can characterize biochemically significant numbers of cells in experimentally reasonable timescales. In principle, computational methods could select based on a vastly larger set of parameters than can be selected by biochemical or pharmacological means, but an unresolved challenge has been how to physically isolate cells of interest from a complex culture. The photostick approach could be used to identify genes whose over- or under-expression affects complex aspects of cell morphology, dynamics, or response to perturbations. This method could also be useful to select antibodies or other functional proteins expressed from a library at one copy per cell. Finally, photostick could be used in the generation of stable cell lines, where gene expression is detected by a morphological or functional parameter rather than fluorescence or antibiotic resistance.

Example 5

Photolift

Reagent

The photocleavable crosslinker, bis-NHS-PC, was synthesized via the procedures shown in FIG. 2. The commercially available compound, 4-[4-(1-Hydroxyethyl)-2-methoxy-5-nitrophenoxy]butanoic acid (1) was first reacted with α,ω-Disuccinimidyl diethylene glycol (2) to give rise of the first product, 3, which was further conjugated with N-hydroxysuccinimide (NHS, 4) in the presence of EDC (N-(3-Dimethylaminopropyl)-N'-ethylcarbodiimide hydrochloride) and the final product "bis-NHS-PC" (5) was produced.

When cells are incubated with the bis-NHS-PC, the two succinimide ester (NHS) arms react with primary amines on the cell surfaces and the substrate. In some instances the crosslinkers bond cells to each other and to the substrate. These crosslinkers are resistant to protease treatment, but labile to violet or near-UV light.

Protocol

Figure 3:
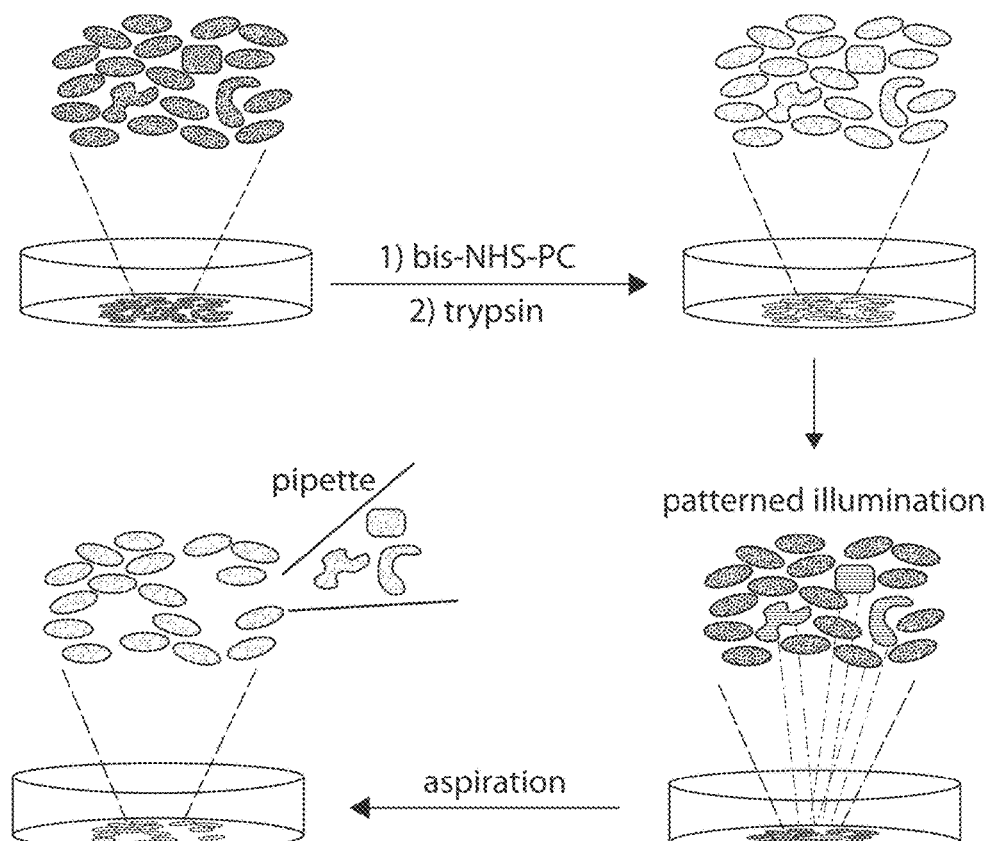
FIG. 3 presents a sequence of steps in the photolift method. Photochemical liberation lifts target cells while others are retained on the dish.

FIG. 3 illustrates the procedures for the photolift protocol. In the photolift protocol, all cells are first nonspecifically crosslinked to each other and to the dish via incubation with the photocleavable crosslinker, bis-NHS-PC (bis-N-hydroxyl succinimide photocleavable compound). A strong protease, trypsin, is then added to cleave all protein-protein bonds linking cells to each other and to the substrate. The cells remain immobilized, however, due to the covalent crosslinker. Illumination with violet light cleaves the crosslinks between the selected cell and its neighbors and the substrate, releasing the cell.

As in the photostick procedure, cells are cultured on glass-bottom dishes coated with fibronectin or other cell adhesion protein. Cell type and cell culture protocol are selected so that a subset of the cells has an attribute of interest, and this attribute is discernable in a microscope. The only constraint on the cell culture is that the cells must not pile on top of each other.

As in the photostick procedure, cells are then imaged to identify those with the feature of interest. The protocol is agnostic to the imaging modality and the modality best suited to the feature of interest should be selected. In certain embodiments, cells are imaged in a custom wide-field optical system comprising a 2× objective with a numerical aperture of 0.5, and fluorescence illumination at 488, 532, and 640 nm. A high-speed scientific CMOS (sCMOS) camera captures images of a wide field of view (4 mm×4 mm) with high spatial (3.25 µm) and high temporal (10 ms) resolutions.

Next, as in the photostick procedure, microscope images are processed to identify cells of interest. The protocol is agnostic to the method of cell identification. In certain embodiments, fluorescence images acquired at two or more times are compared relative to each other to identify cells that exhibited a user-defined temporal pattern of fluorescence.

For photolift methods, the cells are then incubated with 150 µM of bis-NHS-PC in XC buffer (125 mM NaCl, 2 mM KCl, 15 mM HEPES, 30 mM Glucose, 1 mM MgCl2, 2 mM CaCl2) at 37° C. for 3-5 min following by rinsing with XC buffer to remove the unreacted bis-NHS-PC. Next, cells are incubated in XC buffer for another 3-5 min to ensure the crosslinking avidity between cells. The cells are then incubated with protease (typically trypsin) at 37° C. for 10-15 min, followed by a rinse with fresh trypsin. One or more cells are illuminated with light of a wavelength of 365-407 nm at a dose of typically 50 $kJ/cm^2$ (corresponding to 0.5 mW over 10 µm×10 µm for 100 s). The target cell is released from the culture and is aspirated via a glass pipette. The selected cells are further processed, either via further growth, RNA or DNA sequencing, biochemical profiling, or proteomics.

FIGS. 7A to 7D shows exemplary data for photolift, following the protocol outlined above. After treatment with the photolift reagents, a single HEK cell was illuminated with 407 nm light. The cell lifted off the dish and was gently aspirated into the pipette.

REFERENCES

1. D. E. Root, N. Hacohen, W. C. Hahn, E. S. Lander and D. M. Sabatini, Nature methods, 2006, 3, 715-719.
2. J. Moffat, D. A. Grueneberg, X. Yang, S. Y. Kim, A. M. Kloepfer, G. Hinkle, B. Piqani, T. M. Eisenhaure, B. Luo and J. K. Grenier, Cell, 2006, 124, 1283-1298.
3. M. T. Anderson, I. M. Tjioe, M. C. Lorincz, D. R. Parks, L. A. Herzenberg, G. P. Nolan and L. A. Herzenberg, Proc. Natl. Acad. Sci. U.S.A., 1996, 93, 8508-8511.
4. M. R. Emmert-Buck, R. F. Bonner, P. D. Smith, R. F. Chuaqui, Z. Zhuang, S. R. Goldstein, R. A. Weiss and L. A. Liotta, Science, 1996, 274, 998-1001.
5. 5 V. Espina, J. D. Wulfkuhle, V. S. Calvert, A. VanMeter, W. Zhou, G. Coukos, D. H. Geho, E. F. Petricoin and L. A. Liotta, Nature Protocols, 2006, 1, 586-603.
6. M. Henriksen, Nature Methods, 2010, 7.
7. Y. Ozaki, S. Uda, T. H. Saito, J. Chung, H. Kubota and S. Kuroda, PloS one, 2010, 5, e9955.
8. B. P. Fors, J. E. Poelma, M. S. Menyo, M. J. Robb, D. M. Spokoyny, J. W. Kramer, J. H. Waite and C. J. Hawker, J. Am. Chem. Soc., 2013, 135, 14106-14109.
9. T. Matsuda and T. Sugawara, J. Biomed. Mater. Res., 1995, 29, 749-30 756.
10. K. M. El Muslemany, A. A. Twite, A. M. ElSohly, A. C. Obermeyer, R. A. Mathies and M. B. Francis, J. Am. Chem. Soc., 2014.
11. H. Onoe, S. C. Hsiao, E. S. Douglas, Z. J. Gartner, C. R. Bertozzi, M. B. Francis and R. A. Mathies, Langmuir, 2012, 28, 8120-8126.
12. A. M. Kloxin, M. W. Tibbitt and K. S. Anseth, Nature protocols, 2010, 5, 1867-1887.
13. P. Soman, P. H. Chung, A. P. Zhang and S. Chen, Biotechnol. Bioeng., 2013, 110, 3038-3047.
14. K. C. Hribar, P. Soman, J. Warner, P. Chung and S. Chen, Lab on a 40 Chip, 2014, 14, 268-275.
15. D. Shin, J. You, A. Rahimian, T. Vu, C. Siltanen, A. Ehsanipour, G. Stybayeva, J. Sutcliffe and A. Revzin, Angewandte Chemie International Edition, 2014, 53, 8221-8224.
16. M. Tamura, F. Yanagawa, S. Sugiura, T. Takagi, K. Sumaru, H. Matsui and T. Kanamori, Scientific reports, 2014, 4.
17. Y. Kamegaya, W. A. Farinelli, A. V. Vila Echague, H. Akita, J. Gallagher, T. J. Flotte, R. Anderson, R. W. Redmond and I. E. Kochevar, Lasers Surg. Med., 2005, 37, 264-270.
18. M. Yao, A. Yaroslavsky, F. P. Henry, R. W. Redmond and I. E. Kochevar, Lasers Surg. Med., 2010, 42, 123-131.
19. E. Leyva, M. S. Platz, G. Persy and J. Wirz, J. Am. Chem. Soc., 1986, 108, 3783-3790.
20. M. J. Travers, D. C. Cowles, E. P. Clifford and G. B. Ellison, J. Am. Chem. Soc., 1992, 114, 8699-8701.

21. V. Voskresenska, R. M. Wilson, M. Panov, A. N. Tarnovsky, J. A. Krause, S. Vyas, A. H. Winter and C. M. Hadad, *J. Am. Chem. Soc.,* 2009, 131, 11535-11547.
22. M. S. Platz, R. A. Moss and J. Maitland, in *Reviews of reactive intermediate chemistry*, ed. R. S. Sheridan, John Wiley & Sons, 2007, p. 415.
23. A. Reiser, F. Willets, G. Terry, V. Williams and R. Marley, *Transactions of the Faraday Society,* 1968, 64, 3265-3275.
24. MolInspiration, http://www.molinspiration.com/cgi-bin/properties, 2013.
25. D. Sims, A. M. Mendes-Pereira, J. Frankum, D. Burgess, M. Cerone, C. Lombardelli, C. Mitsopoulos, J. Hakas, N. Murugaesu and C. M. Isacke, *Genome Biol.,* 2011, 12, R104.
26. D. R. Hochbaum, Y. Zhao, S. Farhi, N. Klapoetke, C. A. Werley, V. Kapoor, P. Zou, J. M. Kralj, D. Maclaurin, N. Smedemark-Margulies, J. Saulnier, G. Boulting, Y. Cho, M. Melkonian, G. K. Wong, D. J. Harrison, V. N. Murthy, B. Sabatini, E. S. Boyden, R. E. Campbell and A. E. Cohen, *Nat. Methods,* 2014, 11, 825-833.
27. Yamahira, S., Yamaguchi, S., Kawahara, M. & Nagamune, T. Collagen Surfaces Modified with Photo-Cleavable Polyethylene Glycol-Lipid Support Versatile Single-Cell Arrays of Both Non-adherent and Adherent Cells. Macromolecular bioscience (2014).
28. Yang, X. et al. A public genome-scale lentiviral expression library of human ORFs. Nature methods 8, 659-661 (2011).
29. Gilbert, L. A. et al. Genome-scale CRISPR-mediated control of gene repression and activation. Cell 159, 647-661 (2014).
30. Shalem, O. et al. Genome-scale CRISPR-Cas9 knockout screening in human cells. Science 343, 84-87 (2014).
31. Hermanson, G. T. in Bioconjugate techniques (Academic Press, 2013).
32. Goslin, K. in Culturing nerve cells (eds Banker, G. & Goslin, K.) (The MIT Press, Cambridge, Mass., 1998).

EQUIVALENTS AND SCOPE

As used in this specification and the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of selecting cells with features of interest comprising:
   a) providing a culture of cells in a culture dish;
   b) imaging the cells to identify a cell of interest;
   c) adding a photochemical crosslinker comprising a fluorescent dye linked to a radical generator to the culture of cells; and
   d) illuminating the cell of interest with light so that the radical generator produces a radical which covalently cross-links the cell of interest to the surface of the culture dish.

2. The method of claim 1 further comprising washing away cells that are not attached to the surface of the culture dish through the crosslinker.

3. The method of claim 2, wherein the step of washing away cells comprises incubating the culture of cells with an enzyme.

4. The method of claim 3, wherein the enzyme is a proteolytic enzyme.

5. The method of claim 3, wherein the enzyme is an enzyme of marine origin having proteolytic and collagenolytic activity.

6. The method of claim 3, wherein the enzyme istrypsin.

7. The method of claim 1 further comprising isolating the cell of interest from the culture dish.

8. The method of claim 1, wherein the culture dish is coated with cell adhesion proteins.

9. The method of claim 8, wherein the cell adhesion protein is an extracellular matrix protein.

10. The method of claim 9, wherein the extracellular matrix protein is fibronectin, collagen, laminin, fibrillin, vitronectin, thrombospondins, tenascins, entactins (or nidogens), nephronectin, or fibrinogen, osteopontin, agrin, aggrecan, decorin, F-Spondin, matrix extracellular phosphoglycoprotein (MEPE), nidogen-1, testican, poly-L-lysine, poly-D-lysine, poly-L-orinthine, or a combination thereof.

11. The method of claim 1, wherein the step of illuminating the cell of interest comprises using patterned illumination.

12. The method of claim 11, wherein the patterned illumination is performed with a digital micromirror device, galvanometer mirror, acousto-optical beam deflector, or spatial light modulator.

13. The method of claim 1, wherein the step of illuminating the cell of interest comprises illuminating the cell with light having a wavelength of about 360 nm to about 440 nm.

14. The method of claim 1, wherein the step of illuminating the cell of interest comprises illuminating the cell with light having a wavelength of about 440 nm to about 500 nm.

15. The method of claim 1, wherein the step of imaging comprises imaging the cell with a wide-field optical system comprising an objective; a means of illumination; and a camera.

16. The method of claim 15, wherein the means of illumination is fluorescent illumination.

17. The method of 15, wherein the means of illumination utilizes transmitted light.

18. The method of claim 1, wherein the step of imaging is performed with a high-speed camera.

19. The method of claim 1, wherein the step of imaging is performed using epifluorescensce microscopy, confocal microscopy, differential interference contrast microscopy, phase contrast microscopy, or Raman microscopy.

20. The method of claim 1 further comprising continuing to grow the cell of interest.

21. The method of claim 1 further comprising fixing the cell of interest.

22. The method of claim 1 further comprising removing the cell of interest from the culture.

23. The method of claim 1, wherein the cell of interest is subjected to DNA sequencing, RNA sequencing, or proteomic analysis.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 1
gcaagggcga ggagctgttc a                                             21
```

<210> SEQ ID NO 2
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 2
ccgcttgtat agctcgtcca tgcc                                    24

<210> SEQ ID NO 3
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 3
ggaattcggc ttggggatat ccacc                                   25

<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 4
ggcaccacga tgacctcctg c                                       21

<210> SEQ ID NO 5
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 5
gtgagcaagg gcgaggagaa taacat                                  26

<210> SEQ ID NO 6
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 6
ccgcttgtac agctcgtcca tgc                                     23

<210> SEQ ID NO 7
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 7
atcgctctgc aggctggtta cgac                                    24

<210> SEQ ID NO 8
<211> LENGTH: 17
<212> TYPE: DNA
<213> ORGANISM: Artificial Sequence
<220> FEATURE:
<223> OTHER INFORMATION: Synthetic Polynucleotide

```
<400> SEQUENCE: 8
tcggcaccgg cactggg                                                    17
```